United States Patent
Bell et al.

(10) Patent No.: US 7,833,800 B2
(45) Date of Patent: Nov. 16, 2010

(54) THERMAL SENSING WITH BRIDGE CIRCUITRY

(75) Inventors: Alan Bell, Mountain View, CA (US);
Richard H. Bruce, Los Altos, CA (US);
Eric Peeters, Fremont, CA (US);
Michal V. Wolkin, Los Altos, CA (US);
Dirk De Bruyker, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 864 days.

(21) Appl. No.: 11/167,612

(22) Filed: Jun. 27, 2005

(65) Prior Publication Data
US 2005/0254994 A1    Nov. 17, 2005

Related U.S. Application Data

(63) Continuation-in-part of application No. 10/114,611, filed on Apr. 1, 2002, now Pat. No. 7,141,210.

(51) Int. Cl.
*G01N 33/00*   (2006.01)

(52) U.S. Cl. .................. 436/147; 422/51; 422/68.1; 422/99

(58) Field of Classification Search .............. 422/51, 422/68.1, 99; 436/147
See application file for complete search history.

(56) References Cited

U.S. PATENT DOCUMENTS

| | | | |
|---|---|---|---|
| 3,467,501 A | 9/1969 | Groszek | |
| 4,021,307 A | 5/1977 | Mosbach | |
| 4,298,392 A | 11/1981 | Isselmann | |
| 4,731,340 A | 3/1988 | Chang et al. | |
| 4,863,808 A | 9/1989 | Sallo | |

(Continued)

FOREIGN PATENT DOCUMENTS

DE    19947788 A1    4/2001

(Continued)

OTHER PUBLICATIONS

Office communication in U.S. Appl. No. 11/167,748, mailed Feb. 15, 2008, 13 pages, published in PAIR.

(Continued)

*Primary Examiner*—Sam P Siefke
(74) *Attorney, Agent, or Firm*—Mark W. Hrozenchik; Leading-Edge Law Group, PLC

(57) ABSTRACT

Thermal sensing devices can include two subsets of thermal sensors connected in a bridge by circuitry on the same support layer or surface with the sensors. Each thermal sensor can be formed in a patterned layer of semiconductor material, and the bridge circuitry can include leads formed in a patterned layer of conductive material, over or under the semiconductor layer. In one implementation, the bridge circuitry includes conductive portions that extend across and electrically contact the lower surface of each sensor's semiconductor slab. The bridge circuitry can also include pads that can be electrically contacted, such as by pogo pins. The device's reaction surface can be spaced apart from or over the thermal sensors. The device's components can be shaped and positioned so that the bridge's offset voltage is below the sensitivity level required for an application, such as by left-right symmetry about an axis.

33 Claims, 14 Drawing Sheets

U.S. PATENT DOCUMENTS

| | | | |
|---|---|---|---|
| 5,265,417 | A | 11/1993 | Visser et al. |
| 5,312,587 | A | 5/1994 | Templer et al. |
| 5,451,371 | A | 9/1995 | Zanini-Fisher et al. |
| 5,486,337 | A | 1/1996 | Ohkawa |
| 5,805,049 | A | 9/1998 | Yamada et al. |
| 5,813,764 | A | 9/1998 | Visser et al. |
| 5,814,200 | A | 9/1998 | Pethig et al. |
| 5,850,098 | A | 12/1998 | Butler et al. |
| 5,858,306 | A | 1/1999 | Oh et al. |
| 5,924,996 | A | 7/1999 | Cho et al. |
| 5,967,659 | A | 10/1999 | Plotnikov et al. |
| RE36,615 | E | 3/2000 | Wood |
| 6,040,193 | A | 3/2000 | Winkler et al. |
| 6,079,873 | A | 6/2000 | Cavicchi et al. |
| 6,096,559 | A | 8/2000 | Thundat et al. |
| 6,127,914 | A | 10/2000 | Sasaki |
| 6,193,413 | B1 | 2/2001 | Lieberman |
| 6,261,431 | B1 | 7/2001 | Mathies et al. |
| 6,284,113 | B1 | 9/2001 | Bjornson et al. |
| 6,294,063 | B1 | 9/2001 | Becker et al. |
| 6,319,469 | B1 | 11/2001 | Mian et al. |
| 6,331,074 | B1 | 12/2001 | Kimura |
| 6,380,605 | B1 | 4/2002 | Verheagen |
| 6,402,369 | B1 | 6/2002 | Ludington et al. |
| 6,436,346 | B1 | 8/2002 | Doktycz et al. |
| 6,545,334 | B2 | 4/2003 | Verhaegen |
| 6,648,503 | B2 | 11/2003 | Tanaka et al. |
| 6,649,343 | B1 | 11/2003 | Hirota et al. |
| 6,701,774 | B2 | 3/2004 | Srinivasan et al. |
| 6,843,596 | B2 | 1/2005 | Verheagen |
| 6,988,826 | B2 | 1/2006 | Zribi et al. |
| 7,141,210 | B2 | 11/2006 | Bell et al. |
| 7,147,763 | B2 | 12/2006 | Elrod et al. |
| 7,416,897 | B2 | 8/2008 | Bruce et al. |
| 7,419,835 | B2 | 9/2008 | Torres et al. |
| 7,473,030 | B2 | 1/2009 | Bruce et al. |
| 7,473,031 | B2 | 1/2009 | Wolkin et al. |
| 7,521,253 | B2 | 4/2009 | Bruce et al. |
| 7,632,008 | B2 | 12/2009 | Recht et al. |
| 2002/0003830 | A1 | 1/2002 | Tanaka et al. |
| 2002/0021740 | A1 | 2/2002 | Danley |
| 2003/0016725 | A1 | 1/2003 | Whateley et al. |
| 2003/0044800 | A1 | 3/2003 | Connelly et al. |
| 2003/0152128 | A1 | 8/2003 | Verhaegen |
| 2003/0183525 | A1 | 10/2003 | Elrod et al. |
| 2003/0186453 | A1 | 10/2003 | Bell et al. |
| 2003/0186454 | A1 | 10/2003 | Bruce et al. |
| 2003/0186455 | A1 | 10/2003 | Bruce et al. |
| 2004/0038227 | A1 | 2/2004 | Verwaerde et al. |
| 2004/0038228 | A1 | 2/2004 | Verhaegen |
| 2005/0238080 | A1 | 10/2005 | Wolkin et al. |
| 2005/0254552 | A1 | 11/2005 | Bruce et al. |
| 2005/0265898 | A1 | 12/2005 | Bell et al. |
| 2006/0078999 | A1 | 4/2006 | Bell et al. |
| 2006/0132542 | A1 | 6/2006 | Bruyker et al. |
| 2006/0159585 | A1 | 7/2006 | Torres et al. |
| 2007/0145362 | A1 | 6/2007 | Wolkin et al. |
| 2007/0147473 | A1 | 6/2007 | Wolkin et al. |
| 2007/0148416 | A1 | 6/2007 | Wolkin et al. |

FOREIGN PATENT DOCUMENTS

| | | |
|---|---|---|
| WO | WO 99/54730 | 10/1999 |
| WO | WO 00/79254 A1 | 12/2000 |
| WO | WO 01/85978 A2 | 11/2001 |

OTHER PUBLICATIONS

Amendment with Information Disclosure in U.S. Appl. No. 11/167,748, dated Apr. 15, 2008, 15 pages, published in PAIR.

Office communication in U.S. Appl. No. 11/167,748, mailed Jun. 20, 2008, 13 pages, published in PAIR.

Office communication in U.S. Appl. No. 11/167,746, mailed Jan. 17, 2007, 21 pages, published in PAIR.

Amendment after Final Rejection in U.S. Appl. No. 11/167,746, dated Sep. 7, 2007, 13 pages, published in PAIR.

Amendment with Request for Continued Examination in U.S. Appl. No. 11/167,746, submitted Oct. 3, 2007, 12 pages, published in PAIR.

Office communication in U.S. Appl. No. 11/167,746, mailed Dec. 28, 2007, 8 pages, published in PAIR.

Amendment with Information Disclosure in U.S. Appl. No. 11/167,746, dated Mar. 21, 2008, 13 pages, published in PAIR.

Office communication in U.S. Appl. No. 11/167,746, mailed Jun. 27, 2008, 7 pages, published in PAIR.

Torres, F.E., Kuhn, P., De Bruyker, D., Bell, A.G., Wolkin, M.V., Peeters, E., Williamson, J.R., Anderson, G.B., Schmitz, G.P., Recht, M.I., Schweizer, S., Scott, L.G., Ho, J.H., Elrod, S.A., Schultz, P.G., Lerner, R.A., and Bruce, R.H., "Enthalpy arrays", Proceedings of the National Academy of Sciences, vol. 101, No. 26, Jun. 29, 2004, pp. 9517-9522.

"What is a Lock-in Amplifier?", PerkinElmer Instruments Technical Note TN 1000, 2000, pp. 1-4.

U.S. Appl. No. 11/018,757, filed Dec. 2004, pp. 1-21 and 9 sheets of drawings.

Office communication in U.S. Appl. No. 11/167,746, mailed Jul. 9, 2007, 12 pages.

Amendment with Information Disclosure in U.S. Appl. No. 11/167,746, dated Apr. 17, 2007, 21 pages.

Office communication in U.S. Appl. No. 11/167,748, mailed May 11, 2007, 24 pages.

Amendment with Information Disclosure in U.S. Appl. No. 11/167,748, dated Aug. 10, 2007, 16 pages.

Jones, T.B., Gunji, M., Washizu, M., Feldman, M.J., "Dielectrophoretic liquid actuation and nanodroplet formation", Journal of Applied Physics, vol. 89, No. 2, Jan. 15, 2001, pp. 1441-1448.

Washizu, M., "Electrostatic Actuation of Liquid Droplets for Microreactor Applications", IEEE Transactions on Industry Applications. vol. 34, No. 4, Jul./Aug. 1998, pp. 732-737.

Pierce, M.M., Raman, C.S., Nall, B.T., "Isothermal Titration Calorimetry of Protein-Protein Interactions", Methods, vol. 19, 1999, pp. 213-221.

Johannessen, E.A., Weaver, J.M.R., Cobbold, P.H., and Cooper, J.M., "A Suspended Membrane Nanocalorimeter for Ultralow Volume Bioanalysis", IEEE Transactions on Nanobioscience, vol. 1, No. 1, Mar. 2002, pp. 29-36.

Johannessen, E.A., Weaver, J.M.R., Cobbold, P.H., and Cooper, J.M., "Heat conduction nanocalorimeter for pl-scale single cell measurements", Applied Physics Letters, vol. 80, No. 11, Mar. 18, 2002, pp. 2029-2031.

Fominaya, F., Fournier, T., Gandit, P., and Chaussy, J., "Nanocalorimeter for high resolution measurements of low temperature heat capacities of thin films and single crystals", Review of Scientific Instruments, vol. 68, No. 11, Nov. 1997, pp. 4191-4195.

Fowler, J., Moon, H. and Kim, C.-J., "Enhancement of Mixing by Droplet-Based Microfluidics", IEEE, 0-7803-7185-2/02, pp. 97-101.

Pollack, M.G., Fair, R.B., and Shenderov, A.D., "Electrowetting-based actuation of liquid droplets for microfluidic applications", Applied Physics Letters, vol. 77, No. 11, Sep. 11, 2000, pp. 1725-1726.

Office communication in U.S. Appl. No. 11/149,632, mailed Jun. 10, 2008, 11 pages, published in PAIR.

Amendment in U.S. Appl. No. 11/149,632, submitted Sep. 5, 2008, 23 pages, published in PAIR.

Office communication in U.S. Appl. No. 11/149,632, mailed Dec. 8, 2008, 14 pages, published in PAIR.

Request for Reconsideration with Information Disclosure in U.S. Appl. No. 11/149,632, submitted Jan. 6, 2009, 7 pages, published in PAIR.

Office communication in U.S. Appl. No. 11/149,632, mailed Jan. 27, 2009, 10 pages, published in PAIR.

Office communication in U.S. Appl. No. 11/149,632, mailed Jun. 19, 2009, 13 pages, published in PAIR.

Amendment With Request for Continued Examination in U.S. Appl. No. 11/149,632, submitted Apr. 27, 2009, 19 pages, published in PAIR.
Office communication in U.S. Appl. No. 11/167,635, mailed Jun. 11, 2009, 38 pages, published in PAIR.
Amendment in U.S. Appl. No. 11/167,635, submitted Aug. 25, 2009, 24 pages.
Amendment in U.S. Appl. No. 11/149,632, submitted Aug. 25, 2009, 24 pages.
Office communication in U.S. Appl. No. 11/318,975, mailed Apr. 29, 2008, 22 pages.
Amendment with Information Disclosure in U.S. Appl. No. 11/318,975, submitted Jul. 29, 2008, 17 pages.
Office communication in U.S. Appl. No. 11/318,975, mailed Jul. 29, 2008, 3 pages.
Response to Interview Summary in U.S. Appl. No. 11/318,975, submitted Aug. 7, 2008, 4 pages.
Office communication in U.S. Appl. No. 11/318,975, mailed Oct. 15, 2008, 20 pages.
Amendment After Final Rejection in U.S. Appl. No. 11/318,975, submitted Dec. 12, 2008, 12 pages.
Office communication in U.S. Appl. No. 11/318,975, mailed Dec. 24, 2008, 3 pages.
Amendment with Request for Continued Examination in U.S. Appl. No. 11/318,975, submitted Jan. 15, 2009, 23 pages.
Office communication in U.S. Appl. No. 11/318,975, mailed Mar. 6, 2009, 19 pages.
Amendment in U.S. Appl. No. 11/318,975, submitted May 27, 2009, 26 pages.
Office communication in U.S. Appl. No. 11/318,975, mailed Jul. 1, 2009, 18 pages.
Amendment After Final Rejection in U.S. Appl. No. 11/318,975, submitted Jul. 30, 2009, 21 pages.
Office communication in U.S. Appl. No. 11/318,975, mailed Aug. 13, 2009, 7 pages.
Torres, F.E., et al, "Enthalpy arrays", National Academy of Sciences of USA, vol. 101, No. 26, Jun. 29, 2004, 6 pages.
Extended European Search Report, Application No. EP 08157385.9, dated Dec. 17, 2009, 9 pages.
European Patent Application No. EP 1,739,399, filed Jun. 27, 2006, 44 pages.
European Patent Application No. EP 1,533,609, filed Oct. 27, 2004, 25 pages.
European Patent Application No. EP 1,351,052, filed Apr. 1, 2003, 33 pages.
Notice of Allowance and Fee(s) Due in U.S. Appl. No. 11/167,635, mailed Jan. 4, 2010, 9 pages published in PAIR.
Notice of Allowance and Fee(s) Due in U.S. Appl. No. 11/149,632, mailed Dec. 29, 2009, 12 pages, published in PAIR.
Office communication in U.S. Appl. No. 11/318,975, mailed Dec. 8, 2009, 24 pages, published in PAIR.
Amendment in U.S. Appl. No. 11/318,975, submitted Feb. 2, 2010, 29 pages, published in PAIR.
Office communication in U.S. Appl. No. 11/318,926, mailed Oct. 30, 2009, 29 pages, published in PAIR.
Amendment in U.S. Appl. No. 11/318,926, submitted Jan. 26, 2010, 20 pages, published in PAIR.
Amendment with Request for Continued Examination in U.S. Appl. No. 11/318,975, submitted Sep. 25, 2009, 27 pages, published in PAIR.
Office communication in U.S. Appl. No. 11/318,926, mailed Oct. 30, 2009, 29 pages, published in PAIR.
Office communication in U.S. Appl. No. 11/318,967, mailed on Apr. 1, 2010, 30 pages.
Office communication in U.S. Appl. No. 11/318,926, mailed on Apr. 16, 2010, 13 pages.
Office communication in U.S. Appl. No. 11/318,975, mailed on May 10, 2010, 28 pages.

FIG. 11
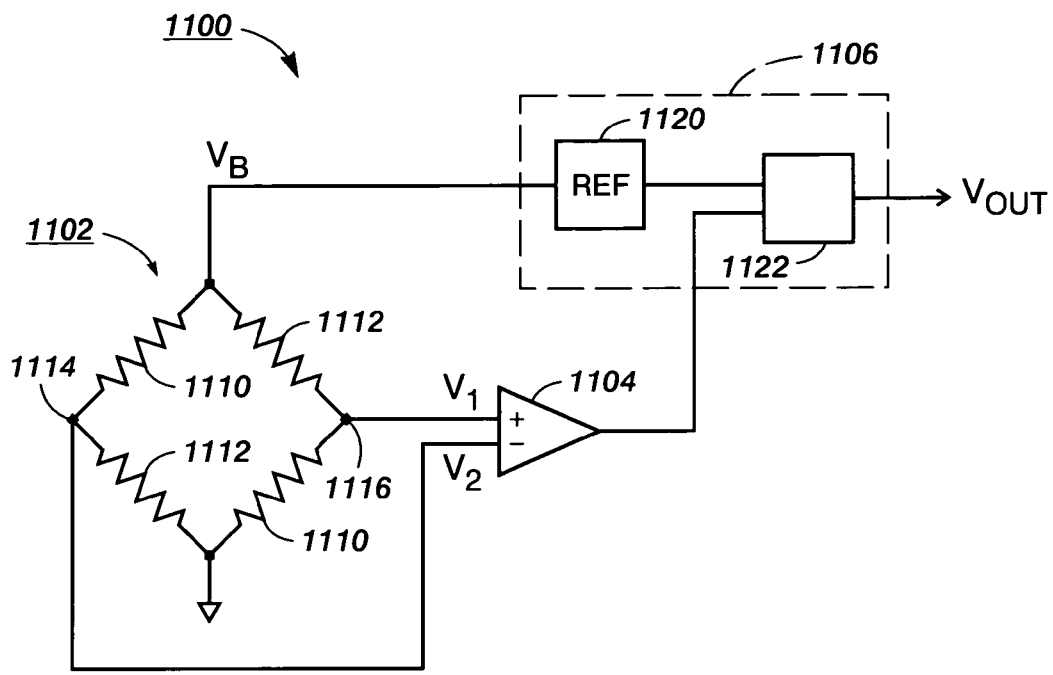
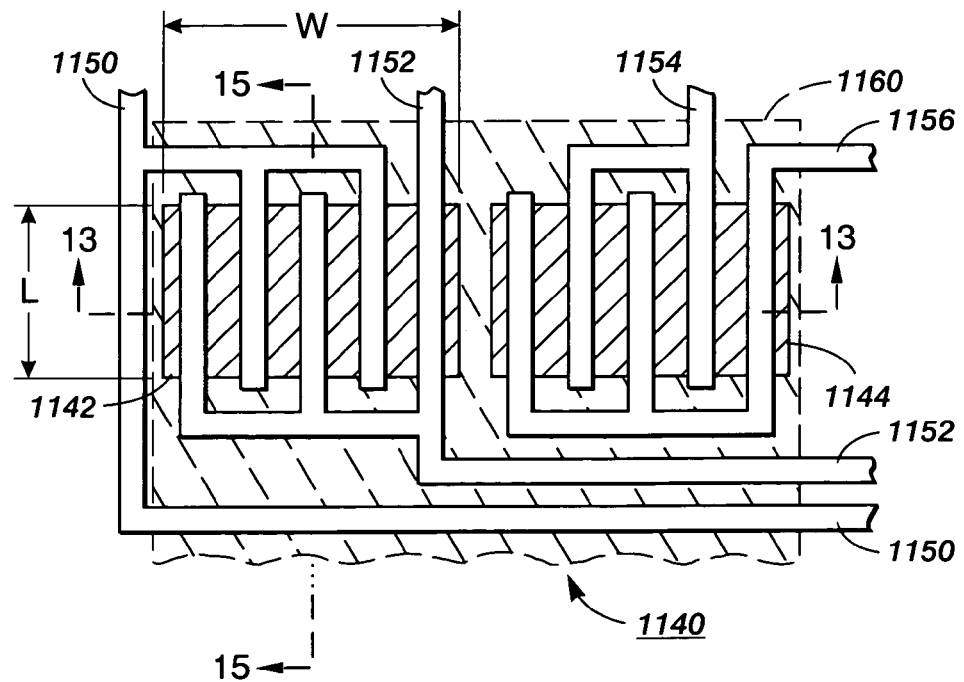
FIG. 12

FIG. 17
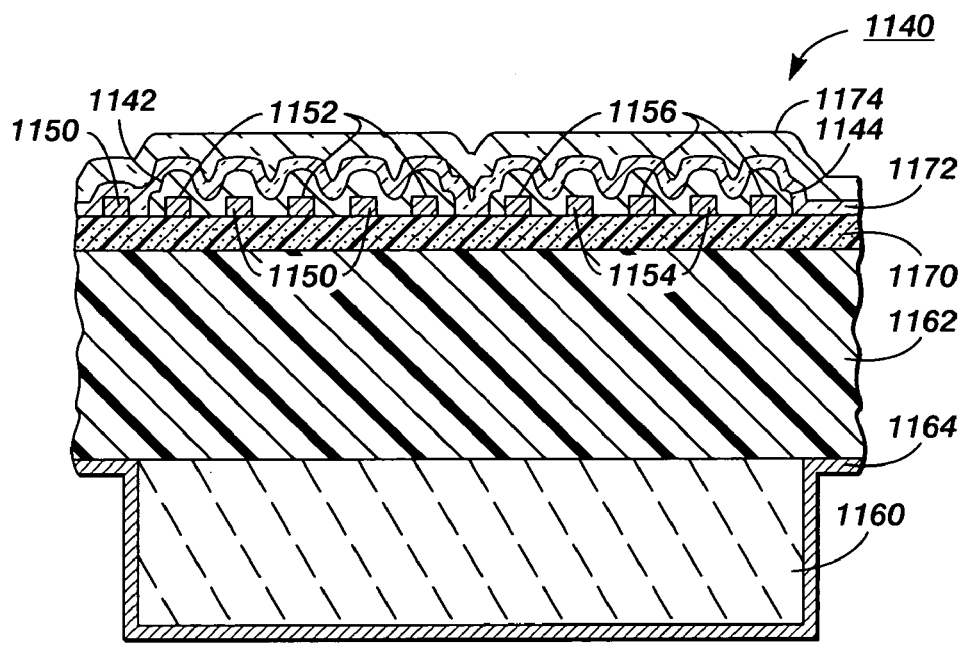
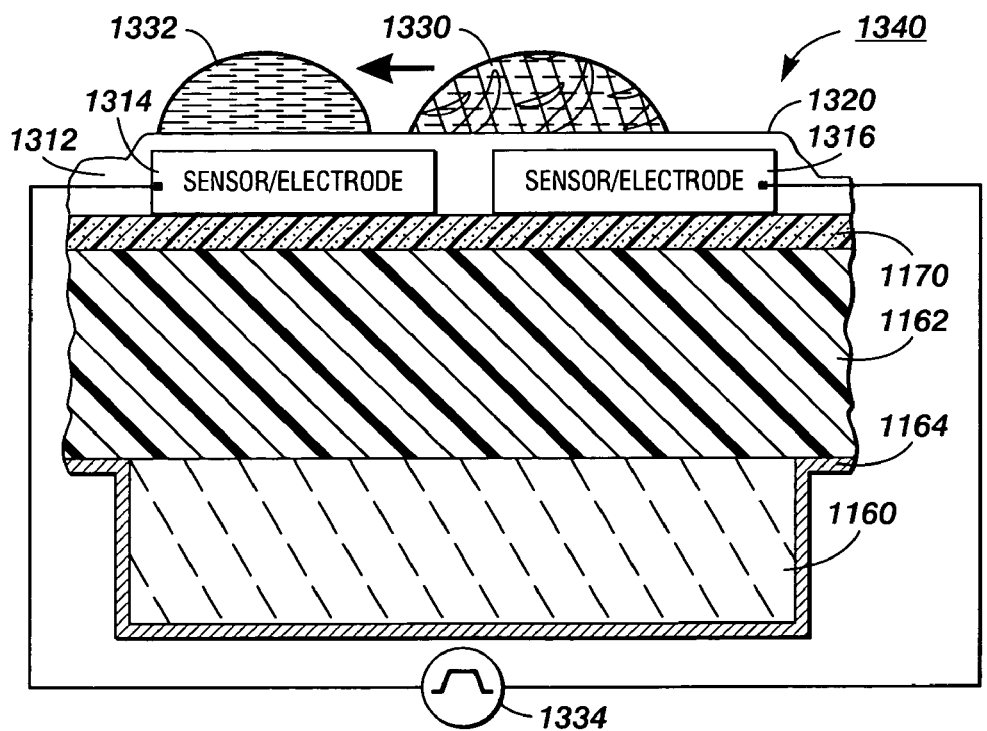
FIG. 18

THERMAL SENSING WITH BRIDGE CIRCUITRY

RELATED APPLICATIONS

This application is a continuation-in-part of U.S. patent application Ser. No. 10/114,611 filed Apr. 1, 2002 now U.S. Pat. No. 7,141,210 (U.S. Patent Application Publication No. 2003/0186453) ("the parent application"), which is incorporated herein by reference in its entirety. Other continuations-in-part of the parent application include U.S. patent application Ser. Nos. 10/303,446 (U.S. Patent Application Publication No. 2003/0186454) and Ser. No. 10/303,500 (U.S. Patent Application Publication No. 2003/0186455), both of which are incorporated herein by reference in their entireties.

BACKGROUND OF THE INVENTION

The present invention relates generally to techniques that sense thermal stimuli. In particular, implementations employ thermometer elements or other thermal sensors connected by bridge circuitry into a bridge. Such bridges can be used, for example, in a calorimeter, a term used herein to refer to any device or apparatus that measures quantities of absorbed or evolved heat or determines specific heats; the use of a calorimeter is referred to herein as calorimetry.

Calorimetry can measure enthalpic changes, including enthalpic changes arising from reactions, phase changes, changes in molecular conformation, temperature variations, and other variations of interest that may occur for a particular specimen. By measuring enthalpic changes over a series of conditions, other thermodynamic variables may be deduced. For example, measurements of enthalpy as a function of temperature reveal the heat capacity of a specimen, and titrations of reacting components can be used to deduce the binding constant and effective stoichiometry for a reaction.

It is known to use bridges in calorimetry and other thermal sensing applications. For example, U.S. Pat. No. 3,467,501 describes a microcalorimeter in which a cell includes measuring thermistors mounted in a solid reactant zone and reference thermistors mounted in a block surrounding the cell; the resistances of the thermistors may be compared by connecting them into a Wheatstone bridge. U.S. Pat. Nos. 4,298,392; 5,312,587; 5,265,417; 5,451,371; and 6,701,774 describe other techniques in which thermistors, other temperature sensitive resistors, or other temperature sensing elements are in a Wheatstone bridge.

Previous techniques in thermal sensing with bridges have a number of limitations. It would be advantageous to have additional techniques for bridges that include thermometer elements or other thermal sensors. In particular, it would be advantageous to have techniques that could be used in very sensitive calorimetry.

SUMMARY OF THE INVENTION

The invention provides various exemplary embodiments, including devices, arrays, and methods. In general, each embodiment involves thermometer elements or other thermal sensors connected in a bridge.

These and other features and advantages of exemplary embodiments of the invention are described below with reference to the accompanying drawings, in which like reference numerals refer to components that are alike or similar in structure or function.

BRIEF DESCRIPTION OF THE DRAWINGS

FIG. 11 is a schematic diagram of a third electronic measuring system that includes resistive thermal sensors.

FIG. 12 is a top plan view of a pair of low noise resistive thermal sensors that can be used in the system of FIG. 11.

FIG. 17 is a cross section of a pair of thermal sensors along the same line as FIG. 13 but in an alternative implementation with layers in a different order.

FIG. 18 is a cross section similar to FIGS. 13 and 17, for an implementation in which semiconductor slabs function both as thermal sensors and drop merging electrodes.

DETAILED DESCRIPTION

Figure 1:
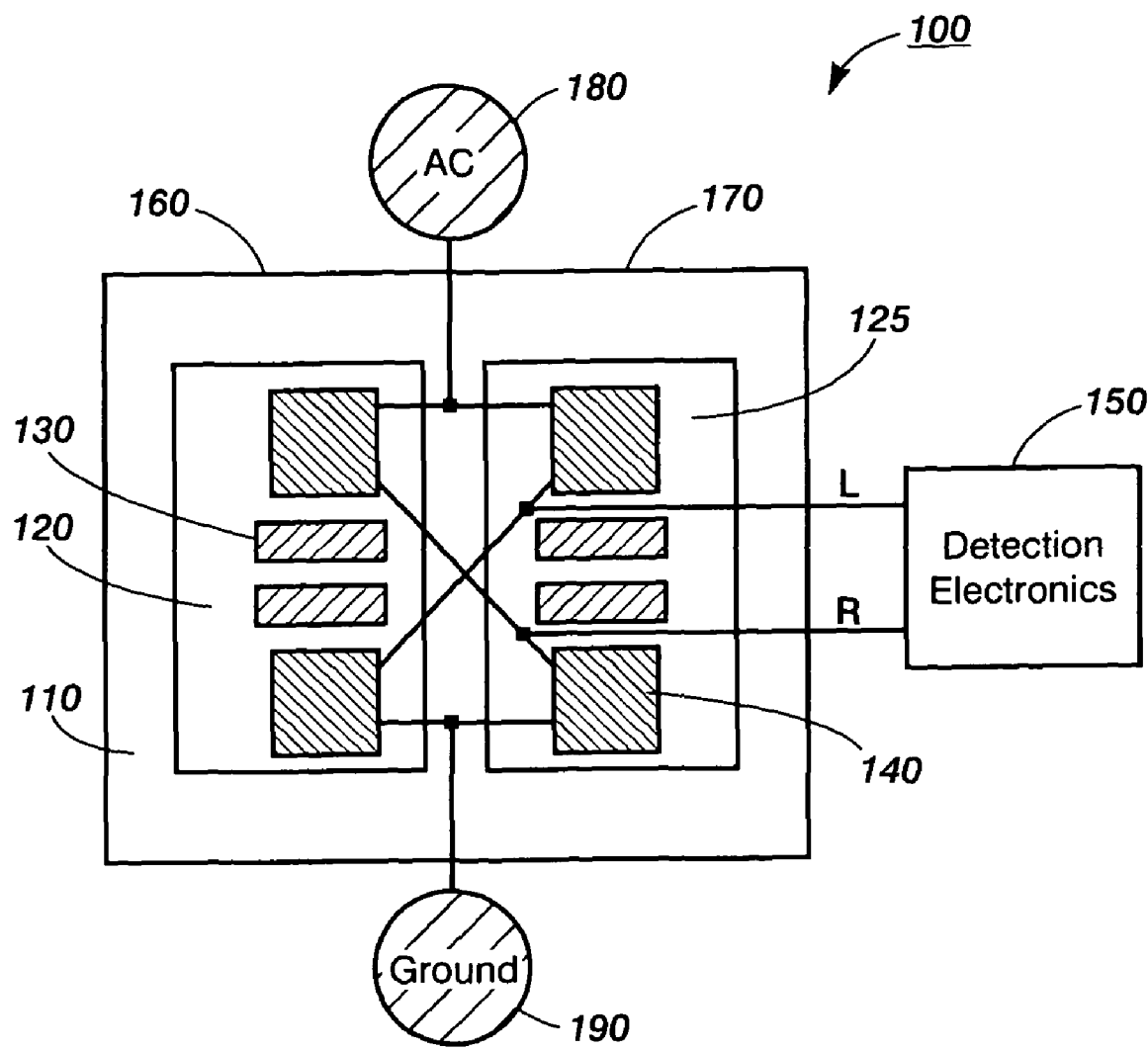
FIG. 1 is a schematic plan view depicting components of a first nanocalorimeter implementation.

The below-described implementations can be applied in measuring thermal effects of chemical reactions as well as in various other ways, some of which are described in the parent application, incorporated herein by reference. In describing some implementations, the terms "target molecule", "ligand", "test ligand", "target protein", and other terms are used herein with substantially the same meanings as set forth in the parent application.

As used herein, the term "thermal change" encompasses the release of energy in the form of heat or the absorption of energy in the form of heat.

As used herein, a "nanocalorimeter" is a calorimeter capable of measuring in the range of nanocalories. Exemplary implementations of the present invention can be applied generally in calorimeters and calorimeter arrays. More specifically, implementations can be applied in nanocalorimeters and nanocalorimeter arrays that enable measurement of enthalpic changes, such as enthalpic changes arising from reactions, phase changes, changes in molecular conformation, and the like. Furthermore, combinatorial methods and high-throughput screening methods can use such nanocalorimeters in the study, discovery, and development of new compounds, materials, chemistries, and chemical processes, as well as high-throughput monitoring of compounds or materials, or high-throughput monitoring of the processes used to synthesize or modify compounds or materials.

Compounds or materials can be identified by the above methods and their therapeutic uses (for diagnostic, preventive or treatment purposes), uses in purification and separation methods, and uses related to their novel physical or chemical properties can then be determined. The parent application, incorporated herein by reference, describes use of high-throughput screening methods and other such techniques in various applications.

Various techniques have been developed for producing structures with one or more dimensions smaller than 1 mm. In particular, some techniques for producing such structures are referred to as "microfabrication." Examples of microfabrication include various techniques for depositing materials such as growth of epitaxial material, sputter deposition, evaporation techniques, plating techniques, spin coating, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes. Also, a support structure could be a "support layer", meaning a layer of material that can support other structures; for example, a support layer could include a polymer film and a barrier layer on a side of the polymer film.

A structure or component is "directly on" a surface when it is both over and in contact with the surface. A structure is "fabricated on" a surface when the structure was produced on or over the surface by microfabrication or similar processes. A process that produces a layer or other accumulation of material over or directly on a substrate's surface can be said to "deposit" the material.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

FIG. 1 shows a plan view of nanocalorimeter detector 100, a first implementation of a detector that can be used in a nanocalorimeter array. This implementation enables a passive thermal equilibration of the combined protein, water, and ligand drops with the device so that the resultant temperature changes can be detected by means of a temperature-sensing device. Suitable thermometer elements are based on thin film materials and include various resistive thermometer elements, resistive thermal sensors, thermistors, and so forth, examples of which are described below.

Because the measurement region is kept small enough and sufficiently thermally conductive, through the use of a thermally conducting layer such as aluminum or copper, the passive equilibration time will be small. As used herein, the terms "thermally conducting" or "thermally conductive" are applicable to any component, layer, or other structure that sufficiently conducts thermal signals from one position or region to another that the thermal signals can affect concurrent thermally sensitive operations in the other position or region. For example, if the thermal signals include information, the information could be available for sensing and electrical detection in the other position or region. Two components are in "thermal contact" even if not in direct contact if a structure between them is conductive for thermal signals of interest. More generally, thermal signals may follow a "thermally conductive path" between two components, meaning a path along which the signals are conducted.

The term "sensing" is used herein in the most generic sense of obtaining information from a physical stimulus; sensing therefore includes actions such as detecting, measuring, and so forth. A "thermal sensor" is accordingly used herein to refer to an element or combination of elements that senses at least one thermal stimulus such as heat, temperature, or random kinetic energy of molecules, atoms, or smaller components of matter. A "resistive thermal sensor" is a thermal sensor with electrical resistance that varies with the thermal stimulus that it senses, in contrast to various thermal sensors that sense in other ways such as with thermocouples or thermopiles. The terms "resistive thermometer element" and "resistive thermometer" similarly refer to an element of any kind with electrical resistance that varies with temperature. As used herein, the term "thermistor" means an electrically resistive component that includes semiconductor material with resistance that varies in response to a thermal change; a thermistor can therefore be employed in a resistive thermal sensor or a resistive thermometer. In each of these definitions, variation in resistance would include both linear and non-linear variations; a non-linear variation might occur in a thermistor, for example if a temperature change causes a phase change in the semiconductor material.

Resistive thermal sensors and resistive thermometers can, for example, be made from materials with a high temperature coefficient of resistivity (TCR) in comparison with those of other materials. Examples of semiconductor materials with high TCR include amorphous silicon, vanadium oxide ($VO_x$), yttrium barium copper oxide (YBCO), and mercury cadmium telluride. Other materials that have been used in resistive thermal sensors include, for example, platinum, nickel, copper, iron-nickel alloys such as balco, tungsten, iridium, oxides of nickel, manganese, iron, cobalt, copper, magnesium, and titanium, and other metals, metal alloys, and oxides of metal. Any such material is referred to herein as a "high TCR material". Furthermore, unless otherwise specified, the terms "vanadium oxide" and "$VO_x$" refer herein to any oxide or combination of oxides of vanadium that can be used in the context, such as $V_2O_5$, $VO_2$, $V_2O_3$, VO, and so forth.

Nanocalorimeter detector 100 includes thermal isolation layer 110, which contains measurement region 160 and reference region 170. Regions 160 and 170 may also be contained in separate isolation regions, as described hereinbelow. Thermal isolation layer 110 provides isolation from surrounding thermal environments, thus increasing measurement time and reducing thermal noise, also referred to herein as Johnson noise, i.e. the theoretical minimum achievable noise level. Although layer 110 is used in this implementation to thermally isolate the reaction and temperature sensing components of the nanocalorimeter detector 100, any means to thermally isolate these components can be used in alternate implementations.

As used herein, the terms "thermal isolation" or "thermal isolating" are applicable to any layer or other structure that sufficiently prevents conduction of or fails to conduct thermal signals from one region to another, so that the thermal signals do not affect concurrent thermally sensitive operations in the other region. A thin layer, for example, may be thermally isolating in its lateral directions, i.e. directions approximately parallel to its surfaces, but may permit thermal conduction in its thickness direction, i.e. the direction perpendicular to its surfaces.

In this implementation, thermal isolation layer 110 may include a plastic material in thin foil form (typically ranging from less than 15 µm to approximately 25 µm in thickness, possibly as thin as 2 µm and as thick as 500 µm for some applications). Candidate plastic materials include polymers such as polyimide (for example DuPont Kapton® and others), polyester (for example DuPont Mylar®, DuPont Teonex® PEN, or DuPont Teijin® Tetoron® PET) foil, PolyEtherEtherKetone (PEEK), or PolyPhenylene Sulphide (PPS). Alternatively, thermal isolation layer 110 includes other thin layers of sufficiently low thermal conductivity, such as SiN and comparable materials.

Measurement region 160 and reference region 170 include thermal equilibrium regions 120 and 125 respectively, that are thermally isolated from the detector's mechanical support. In this implementation, thermal equilibrium region 120 contains two resistive thermometers 140, which measure the reaction temperature, while thermal equilibrium region 125 contains a second set of two resistive thermometers 140, which measure the variations in the background temperature. Resistive thermometers 140 can therefore be produced in thermal equilibrium regions 120 and 125 using microfabrication or other techniques, such as printed circuit board fabrication techniques.

As used herein, the term "reaction region" refers to a region in which a reaction can occur, producing thermal change. A "reaction surface" is a part of a surface that is a reaction region. Both thermal equilibrium regions 120 and 125 are reaction regions and, more specifically, reaction surfaces because they are sufficiently large to receive and support separate drops of protein and ligand deposited by direct printing and also to support the combination of these two drops after merging, triggered by an example drop merging device 130. For example, for a 400 nl final drop size, the detector, which includes the measurement and reference regions, may be 3.7 mm by 4.6 mm. Each thermal equilibrium region 120 and 125 has sufficient thermal conduction for the region to equilibrate quickly relative to thermal dissipation. The regions each have a sufficiently low heat capacity such that little of the heat of reaction is absorbed in the support. High thermal conductivity with low heat capacity may be accomplished, for example, with a metal film such as a 10 µm thick aluminum or copper film extending over the area of the thermal equilibrium region. In this example, for a 400 nl drop and a 10 µm thick aluminum film, the film absorbs approximately 7% of the heat of reaction. In general, the term "high thermal conductivity" refers herein to a thermal conductivity that is approximately as great or greater than those of aluminum and copper.

As suggested above, in this implementation, the thermal equilibrium regions 120 and 125 must be thermally isolated from their environment so that the temperature difference caused by the reaction takes a relatively long time to dissipate. The longer this dissipation time, the longer the signal can be integrated during measurement, which improves the signal to noise ratio. For example, a 10 second integration time corresponds to a 0.1 Hz measurement bandwidth and increases the signal to noise ratio by 3.2 over a 1 second integration. Thermal dissipation can occur through at least four different channels: conduction across the supporting medium, conduction through the electrical interconnect, conduction through the surrounding environment and evaporation. For the example of conduction across the thermal isolation layer 110, the rate of heat transfer from the drop equals the thermal conductivity of the layer 110 multiplied by the cross section of the layer 110 through which the heat is conducted and the temperature gradient across the region, or $Q=\Lambda A dT/dx$, where $\Lambda$ is the thermal conductivity of thermal isolation layer 110, A is the cross section of the region through which the heat is conducted and dT/dx is the temperature gradient across thermal isolation layer 110. Note Q=C dT/dt where C is the heat capacity of the drop, and from this $T=T_o e^{-\Lambda At/CL}$, where t is the time, L is the length of the isolation layer 110, and all temperatures are relative to the temperature of the surrounding environment, with the approximation dT/dx=T/L. The time constant, $\tau$, for thermal dissipation is therefore $\tau = CL/\Lambda A$.

Consequently, the time constant increases with increases in the heat capacity of the drop and decreases with increases in the rate of thermal conduction. Note that while the heat capacity of the drop increases with drop size, increasing the drop size reduces the density of detectors on an array of detectors, increases the thermal equilibration time for the drop, and uses valuable material. A lower array density means a larger array size for a given detector number.

In the example implementation, drop size is 400 nl for the combined drop after merging. For this drop size, estimates of the time constants associated with different dissipation channels in one implementation are shown in the following Table 1:

TABLE 1

| Conduction Channel | Time Constant |
|---|---|
| Conduction across support layer + interconnect leads | 110 sec |
| Conduction through vapor (air) | 6 sec |
| Evaporation (25° C. operation) | 8 sec |

For the purposes of Table 1, it was assumed that the thermal isolation layer is 7 µm thick plastic and there are eleven interconnect leads with thickness of 0.1 µm for each thermal equilibrium region. As mentioned above, the thermal isolation layer for this example implementation may be fabricated of a plastic material in thin foil form (typically ranging from less than 15 µm to approximately 25 µm in thickness for this implementation, possibly as thin as 2 µm and as thick as 500 µm for some applications), thereby ensuring that the above time constant for conduction across the thermal isolation layer is large compared with the measurement bandwidth. Examples of candidate plastic materials include polyimide (for example Dupont Kapton®. and others), polyester (for example Dupont Mylar®, DuPont Teonex® PEN, or DuPont Teijin® Tetoron® PET) foil, PolyEtherEtherKetone (PEEK), PolyPhenylene Sulphide (PPS), polyethylene, or polypropylene. Rather than air, the vapor could be any appropriate gas or combination of gasses, such as argon or possibly xenon.

In the implementation of FIG. 1, the same material may be used for the support and the thermal equilibration, including the resistive thermometers. Consequently, one important consideration in selecting a substrate polymer is the highest temperature that is needed in subsequent deposition and processing of thermometer, conductor and insulator films in the particular implementation. As an example, the temperature needed in the deposition of amorphous silicon thermometer material is typically in the range of 170-250° C. This requires the selection of a substrate polymer film with a high softening temperature. These polymers may include, but are not limited to, polyimide, PolyEtherEtherKetone (PEEK), or PolyPhenylene Sulphide (PPS). Conversely, deposition of vanadium oxide thermometer material can be done at a substantially lower temperature such as room temperature. This allows the selection of substrate polymers with a lower softening point, such as polyester (Dupont Mylar® or DuPont Teonex® PEN).

These plastic substrates enable low cost manufacturing that can scale to large arrays of detectors, which enable fast and cost effective testing of large numbers of reactions. Detectors as in FIG. 1 could be used, for example, in detector array sizes of 96, 384, 1536 and larger. The low-cost detector arrays might also be used once and then discarded, eliminating time-consuming washing steps and reducing problems with cross-contamination.

Another thermal consideration is the characteristic time for a drop to equilibrate with the detector after it is placed on the detector. This is a combination of the characteristic time for conduction of heat through the drop, $t_1$, and the characteristic conduction time across the detector, $t_2$. In an implementation, an aluminum film is used to increase the thermal conduction across the detector. An estimate of the characteristic time $t_1$ is $$t_1 = 0.44 R^2/\alpha \approx 0.6 \text{ sec},$$

where R is the drop radius, in this example 460 μm, and α is the thermal diffusivity of the drop, 0.0015 cm²/sec for water. For thin plastic substrates, the characteristic time for lateral conduction across the detector is governed by conduction across the metal film incorporated into the design for temperature equilibration, which is an aluminum strip in this example. An estimate for this characteristic time is $$t_2 = (\rho C_p V)_{drop} \times L_{Al}/4R_{drop} \times \delta \times k_{Al} \approx 0.4 \text{ sec},$$

where ρ is the density of the drop, 1 g/cm³ in this example; $C_P$ is the specific heat, 1 cal/gK in this example; $L_{Al}$ is the length of the conduction path along the aluminum strip from one drop to the other, 2.5 $R_{drop}$ in this example; δ is the aluminum strip thickness, 10 μm in this example; and $k_{Al}$ is the aluminum thermal conductivity, 0.57 cal/K-cm-sec. The aluminum thickness is selected to provide sufficient thermal conduction without contributing significantly to the heat capacity of the detector. Heat capacity of the detector must be made sufficiently low so as to minimize the absorption of heat released from the reaction in the drop in order to minimize attenuation of the temperature change arising from the reaction.

Each thermal equilibrium region 120 and 125 contains thermometers 140 and drop merging electrodes 130. Although for the purposes herein thermometers 140 are shown spaced apart from more centrally-positioned drop merging electrodes 130 on each thermal equilibrium region 120 and 125, this configuration is for means of example only. Provided that the drop merging device 130 and thermometers 140 are in good thermal contact with the high conductance film, the exact placement of thermometers 140 and drop merging electrodes 130 is not important for thermal considerations.

In operation, the two resistive thermometers 140 situated in thermal equilibrium region 120 detect the heat of reaction between an arbitrary protein and a ligand at low concentrations deposited within thermal equilibrium region 120. In this example, the heat of reaction is detected through measurement of a voltage change in a bridge circuit due to the resistance change in the thermometers that are configured in the bridge circuit. This is an example of connecting or interconnecting circuitry that allows "electrical detection" of an event or characteristic, such as detection of temperature or thermal signals or of a difference between two voltages, resistances, or temperatures, meaning that the circuitry provides or can be connected to circuitry that provides an electrical signal indicating the detected event or characteristic. Within any circuitry, electrically conductive components that serve primarily to connect other components are referred to herein as "leads" or "lines."

As used herein, the term "bridge" refers to any electrical instrument or network for measuring or comparing resistances, inductances, capacitances, or impedances by comparing two voltages to each other or by comparing their ratio to a known ratio. Further, the terms "bridge circuit" and "bridge circuitry" refer to circuits and circuitry that connect or interconnect resistive elements or other elements so that they can be used in a bridge. Bridge circuitry is "capable of being driven to allow electrical detection" of a characteristic, such as detection of a difference between two voltages, resistances, or temperatures, if the bridge circuitry is or can be connected to receive drive signals and also is or can be connected to circuitry that provides an electrical signal indicating the detected characteristic when the bridge circuitry is receiving the drive signals.

Resistive thermometers 140 in thermal equilibrium region 120 detect a reaction between a sample ligand and a protein; the other resistive thermometers 140 in thermal equilibrium region 125 serve as a reference. Because the temperature rise due to the reaction may be small, for example approximately 10 μK for protein and ligand concentrations of 1 μM and a heat of reaction of $10^4$ cal/mole, the resistive thermometers 140 are fabricated from materials that provide a large change in resistance for a small temperature change.

In this implementation, the resistive thermometers 140 are fabricated from high TCR material. Similar small drops of non-reactive solution (for example water or mixtures of water and DMSO) and target protein, the control combination, are deposited close together in thermal equilibrium region 125. Resistive thermometers 140 are configured as an AC bridge represented by AC generator 180 and ground 190, discussed in more detail hereinbelow. At a specified time after the drops have reached thermal equilibrium, they are moved together to initiate the reaction. The movement operation creates sufficient mixing of the two drops in a time small compared to the measurement time. The heat released by the protein-ligand reaction of the test combination causes a change in the resistance of the affected thermometers relative to the reference thermometers. This change in resistance causes the voltage at the detection point to change from zero. This change is detected by sensitive, noise rejecting circuits such as a lock-in amplifier within detection electronics 150.

Figure 2:
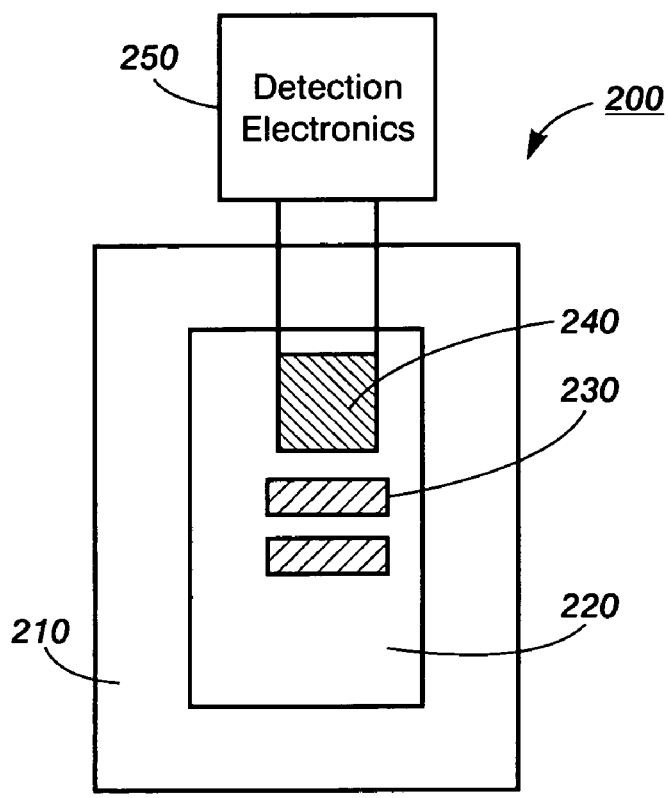
FIG. 2 is a schematic plan view depicting components of a second nanocalorimeter implementation.
Figure 3:
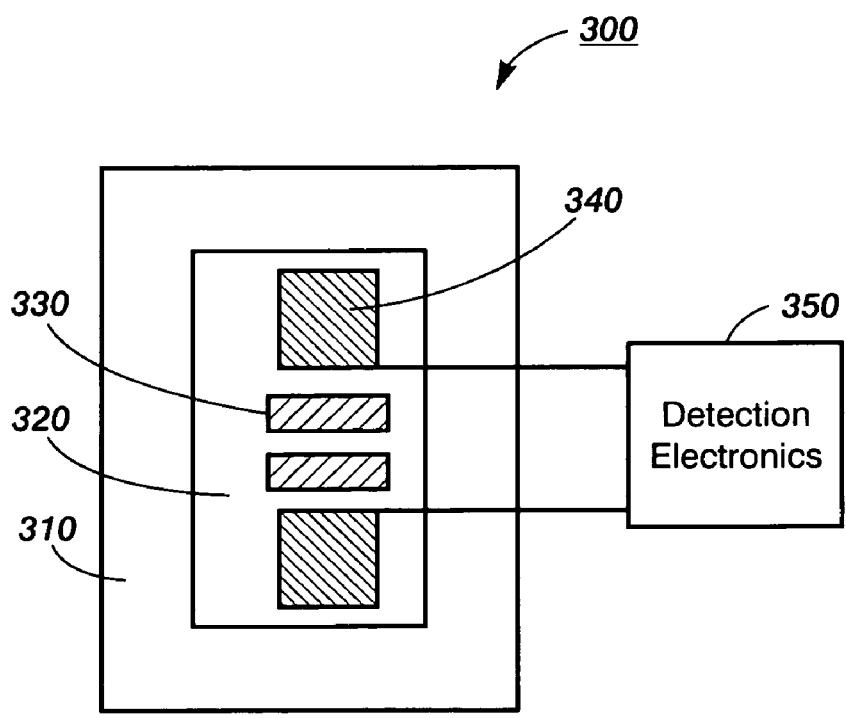
FIG. 3 is a schematic plan view depicting components of a third nanocalorimeter implementation.
Figure 4:
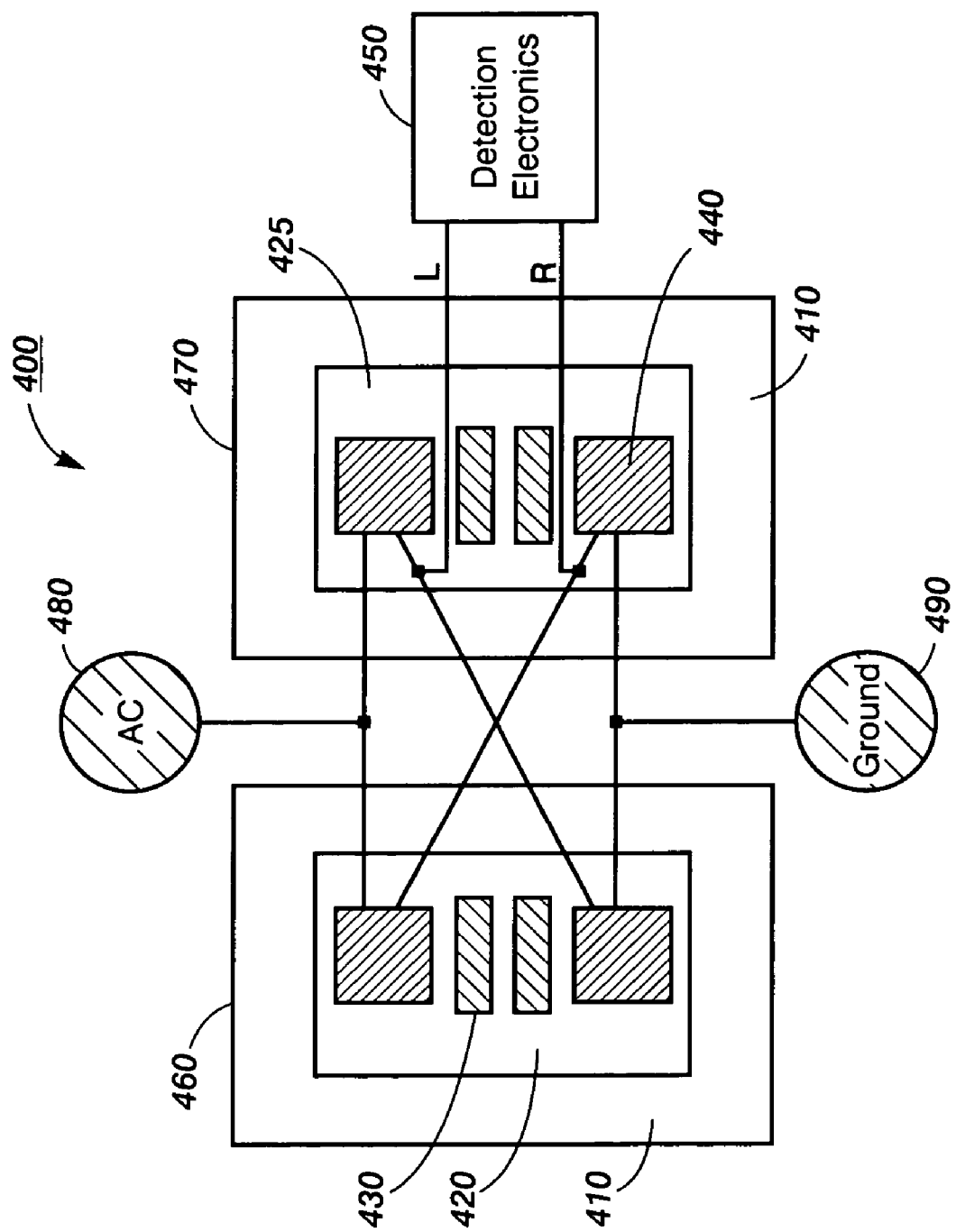
FIG. 4 is a schematic plan view depicting components of a fourth nanocalorimeter implementation.

FIGS. 2-4 show other implementations in which nanocalorimeter detectors 200, 300, and 400 include thermal isolation layers 210, 310, and 410, respectively, which contain thermal equilibrium regions 220, 320, 420, and 425. Thermal isolation layers 210, 310, and 410 provide isolation from surrounding thermal environments, thus increasing measurement time and reducing thermal noise.

In FIG. 2, thermal equilibrium region 220 contains one resistive thermometer 240, which measures the reaction temperature. In FIG. 3, thermal equilibrium region 320 contains two resistive thermometers 340, which measure the reaction temperature. In FIG. 4, thermal equilibrium regions 420 and 425 each contain two resistive thermometers 440, which measure the reaction temperature. Each resistive thermometer is produced in thermal equilibrium region 220, 320, 420, or 425 using microfabrication or other techniques, such as printed circuit board fabrication techniques.

Thermal equilibrium regions 220, 320, 420, and 425 are each sufficiently large to receive and support separate drops of protein and ligand deposited by direct printing and also to support the combination of these two drops after merging, triggered by drop merging device 230, 330, or 430. Thermal equilibrium regions 220, 320, 420, and 425 each have a sufficient thermal conduction for the region to equilibrate quickly relative to the thermal dissipation. Each region also has a sufficiently low heat capacity such that little of the heat of reaction is absorbed in the support. High thermal conductivity with low heat capacity may be accomplished, for example, with a metal film such as a 10 μm thick aluminum or copper film.

In addition to resistive thermometers, thermal equilibrium regions 220, 320, 420, and 425 contain drop merging devices 230, 330, and 430, respectively. Although thermometers 240, 340, and 440 are shown spaced apart from more centrally-positioned drop merging devices 230, 330, and 430 on thermal equilibrium regions 220, 320, 420, and 425, this configuration is for example only. Provided that the drop merging device 230, 330, or 430 and thermometer 240, 340, or 440 are in good thermal contact with the high conductance film, the exact placement of thermometer 240, 340, or 440 and drop merging device 230, 330, or 430 is not important for thermal considerations.

In operation, resistive thermometers 240, 340, and 440 situated in thermal equilibrium regions 220, 320, 420, and 425 detect the heat of reaction between reactants such as an arbitrary protein and a ligand at low concentrations deposited within thermal equilibrium regions 220, 320, 420, and 425, respectively. For example, resistive thermometers 440 situated in thermal equilibrium region 420 detect the temperature of drops deposited and merged within thermal equilibrium region 420. Similar small drops of non-reactive solution (for example water or mixtures of water and DMSO) and target protein, the control combination, are deposited close together in thermal equilibrium region 425. In this example, the heat of reaction is detected through measurement of a voltage change in a bridge circuit due to the resistance change in the thermometers, which are configured in the bridge circuit.

In general, resistive thermometers 240, 340, and 440 in thermal equilibrium regions 220, 320, and 420 detect a reaction between a sample ligand and a protein or between other suitable reactants, while resistive thermometers 440 in region 425 detect a reference reaction, such as between non-reacting fluids. Because the temperature rise due to the reaction may be small (approximately 1 mK for the implementation of FIG. 2 or, in other implementations, approximately 10 μK for protein and ligand concentrations of 1 μM and a heat of reaction of $10^4$ cal/mole), resistive thermometers 240, 340, and 440 are fabricated from material that provides a large change in resistance for a small temperature change. In these implementations, resistive thermometers 240, 340, and 440 are made of high TCR material.

Resistive thermometers 240 and 340 are each configured as one leg of an AC bridge, the other legs of which (i.e. any legs without resistive thermometers) are included in detection electronics 250. Other legs of the bridge are made, for example, of low temperature coefficient resistors located on an amplifier printed circuit board (PCB). Similarly, resistive thermometers 440 are configured as legs of an AC-biased Wheatstone bridge, driven between AC generator 480 and ground 490, discussed in more detail hereinbelow.

At a specified time after the drops have reached thermal equilibrium, they are moved together to initiate the reaction. The movement operation creates sufficient mixing of two drops in a time small compared to the measurement time. The heat released by the protein-ligand reaction of a test combination causes a change in the resistance of affected thermometers. This change in resistance causes voltage at a detection point to change from zero. This change is detected by sensitive, noise rejecting circuitry such as a lock-in amplifier. Alternatively if the reactions to be measured produce enough heat, the resistance change of one or more thermometers could be measured by a direct DC resistance measurement, such as through two thermometers connected in series.

Figure 5:
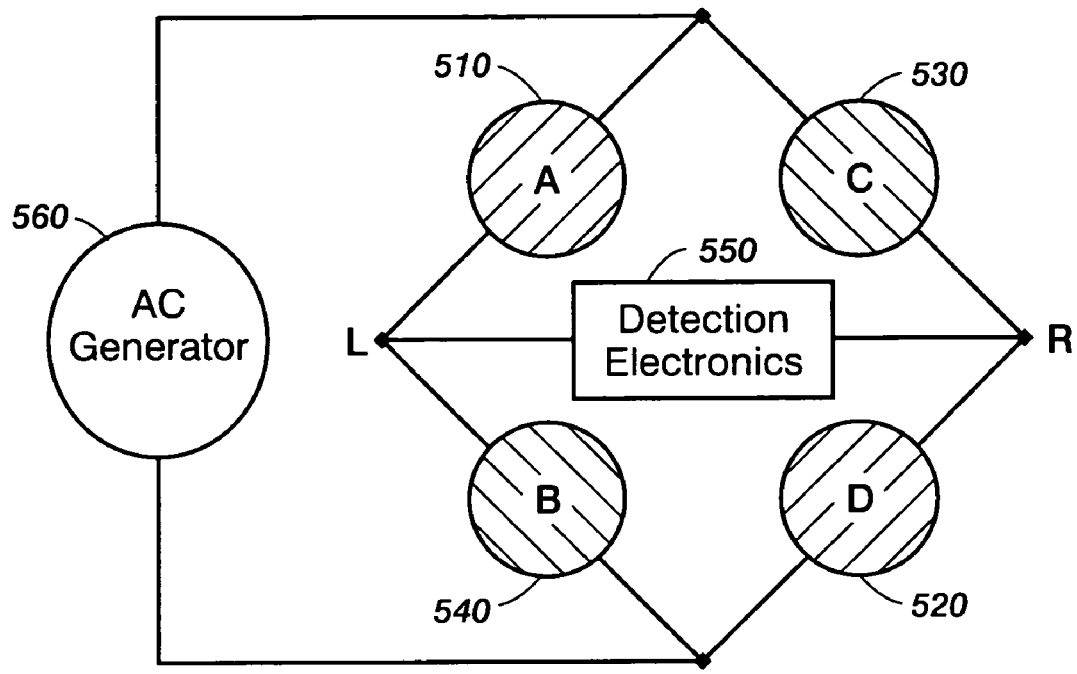
FIG. 5 is a schematic circuit diagram of a first electronic measuring system with resistive thermometer elements.

FIG. 5 shows thermometers 510, 520, 530 and 540 forming four resistive legs of one example configuration for a bridge circuit. Resistive thermometers simultaneously measure temperature changes due to both the reaction and the background drift. In this example, two measurement thermometers 530 and 540 measure the reaction and two reference thermometers 510 and 520 measure the background temperature changes. If the resistance of the measurement thermometers changes, as happens when the temperature in the measurement region increases, then the voltage at output detection point R in the bridge becomes more positive or negative relative to ground, depending on the polarity of the voltage placed across the bridge circuit and the sign of the TCR, while the voltage at output detection point L in the bridge does the opposite, that is, becomes less positive or negative relative to ground, respectively. This configuration maximizes the voltage difference across detection electronics 550. As will be appreciated by one skilled in the art, other bridge configurations are possible, such as one in which thermometer 540 has a low temperature sensitivity and is not fabricated on the device or where thermometer 520 is replaced by a variable resistor used to balance the bridge and is also not fabricated on the device.

Resistance thermometers 510, 520, 530 and 540 may be fabricated from patterned thin film and are connected as a bridge. The resistance of each thermometer varies with temperature by an amount proportional to the TCR of the material used. Since $\alpha = 1/R(\Delta R/\Delta T)$, it follows that $\Delta R = \alpha R \Delta T$, where R is resistance, T is temperature, and α is the TCR of the thermometer material. Therefore, the signal voltage across the resistor varies by $$\Delta V_S = \Delta RI = \alpha R \Delta T \sqrt{\frac{P}{R}},$$

where $V_S$ is the signal voltage, I is the current through the resistor, and P is power. The thermal noise in each resistor becomes $$V_N = \sqrt{4kTRB} = 1.2 \times 10^{-10} \sqrt{RB}$$

where B is the measurement bandwidth in seconds, R is the resistance in Ohms, and k is Boltzmann's constant. Assuming the detection system can be constructed without introducing noise in excess of the thermal noise, the signal to noise ratio becomes $$S/N \cong 8.3 \times 10^9 \alpha \Delta T \sqrt{P/B}.$$

Protein-ligand reactions are generally investigated at low concentrations during high-throughput screening, typically in the range of $10^{-5}$ to $10^{-6}$ M. The reactions typically release a heat of reaction, Q, which is on the order of $10^4$ cal/mole. For illustrative purposes, consider combining two drops with concentrations of 2 µM of protein and ligand, respectively. If the drops have equal volumes, the combination has a 1 µM concentration of each reactant. Additionally, $$CV\Delta T = MVQ,$$

where V is the solution volume, C is the heat capacity of the solution, and M is the concentration in the mixed drop. Therefore, $$\Delta T = MQ/C = 10^{-6} \text{ mole}/L \times 10^4 \text{ cal/mole}/10^3 \text{ cal/K-L} = 10^{-5} \text{ K},$$

where Q is the heat of reaction, C is the heat capacity of the solute, and M is the concentration in the mixed drop.

For example, for a thin film thermometer made from a-Si, for which $\alpha = 2.8 \times 10^{-2}$ K$^{-1}$, and a bandwidth of 0.1 Hz, a signal to noise ratio of 7 is achieved with 1 µW of power dissipated in the resistor. The voltage change then becomes $$\Delta V_S = 2\Delta RI = 2\alpha \Delta TRI = 4 \times 10^{-7} RI \cong 4 \times 10^{-7} \sqrt{PR}.$$

Table 2 of the parent application, incorporated herein by reference, provides the signal strength for various exemplary combinations of thermometer impedance and power. In current implementations, thermometer impedances are approximately 8 kΩ.

FIGS. 1-5 illustrate examples of devices, each of which includes a support layer. Two or more resistive thermometer elements are on the support layer, together with bridge circuitry. The bridge circuitry electrically connects first and second subsets of the thermometer elements in a bridge, and the bridge circuitry has one or more detection points. The bridge circuitry is capable of being driven to allow electrical detection, at the detection points, of differences between first and second temperature changes. The first temperature change is received by the first subset of the thermometer elements and the second temperature change is received by the second subset of the thermometer elements.

The techniques described above for implementing the devices shown in FIGS. 1-5 also illustrate a method of producing detecting devices. The method includes producing resistive thermometer elements and bridge circuitry as described above. In particular, the thermometer elements and the bridge circuitry are produced on a support layer.

To initiate a reaction, the deposited drops need to be merged together and the drop contents well mixed. It is noted that numerous methods for drop deposition are known in the art, any of which may operate beneficially for the purpose of dispersing drops.

Although numerous means and methods for merging the deposited drops may be utilized, for the purposes herein, the exemplary methods disclosed in co-pending U.S. patent application Ser. No. 10/115,336 (U.S. Patent Application Publication No. 2003/0183525), entitled "Apparatus and Method for Using Electrostatic Force to Cause Fluid Movement", incorporated herein by reference, will be briefly described. To reduce complexity of the system and to increase reliability, this example drop merging method utilizes electrostatic forces generated by a planar configuration of two electrodes to merge the two drops and cause equilibration through fast mixing. The electrodes can be thin conducting films produced on the surface of the device using microfabrication or other techniques, such as printed circuit board fabrication techniques.

Figure 6:
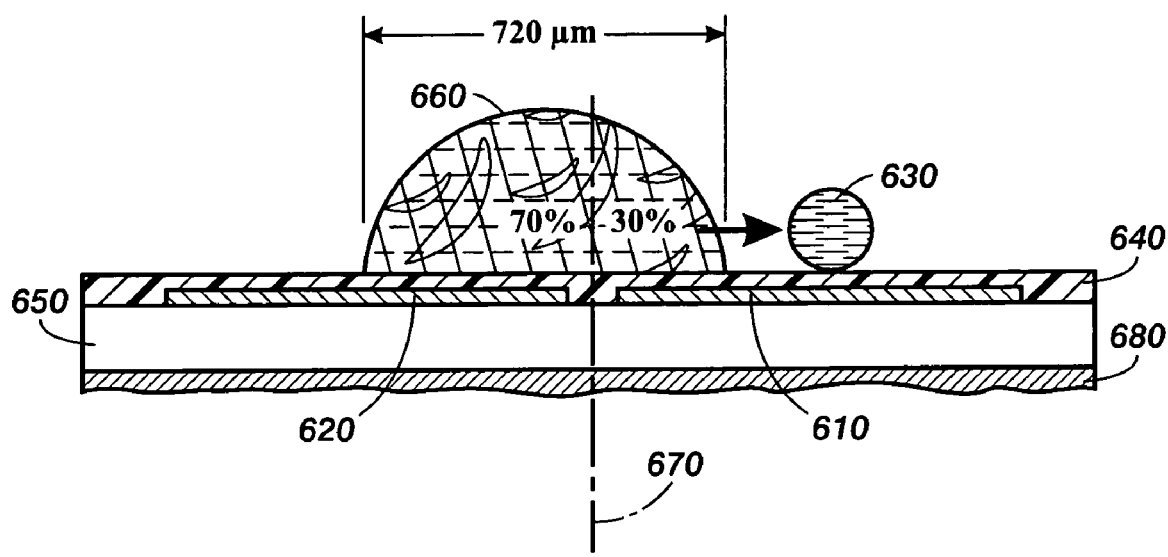
FIG. 6 is a schematic cross-section showing merging of deposited drops on a nanocalorimeter, such as in one of FIGS. 1-4.

FIG. 6 shows merging electrodes formed from conducting films 610 and 620, which are positioned on the surface of substrate 650 and covered by insulating layer 640. In this example, conducting films 610 and 620 may be approximately 1.0 mm by 0.8 mm in size, with a thickness ranging in size from approximately 0.1 µm to approximately 10 µm, and are separated by a gap of approximately 50 µm and are made of a thin film of aluminum, copper, chromium, titanium-tungsten (TiW), or a combination of them; the insulating layer may be approximately 0.1 µm to approximately 2 µm in thickness and may, for example, be made of silicon oxide or silicon nitride or silicon oxynitride, or spin-, spray-, or otherwise deposited polymers, such as parylene, Dupont Teflon® AF, 3M™ Fluorad™ products, 3M™ EGC 1700, other fluoropolymers, polysiloxanes, diamond-like carbon or other spin-coated, spray-coated, dip coated, or vapor deposited polymers. Suitable insulator materials have a high electrical resistivity, chemical and mechanical durability and have no pinholes in deposited thin film form. High conductance film 680 enables thermal equilibration in the thermal equilibrium region. Protein drop 660 is deposited asymmetrically across the surface above conducting films 610 and 620 such that the drop disproportionately occupies the surface above one of the conducting films. In this example, 70% of protein drop 660 occupies the surface on the side of meridian 670 above conducting film 620 and 30% of protein drop 660 occupies the surface on the side of meridian 670 above conducting film 610.

Ligand drop 630 is deposited on the surface above conducting film 610. When a voltage is applied, such as in the form of a voltage pulse, across conducting films 610 and 620, drop 660 is propelled toward stationary drop 630 and the drops merge. While the comparative drop sizes of protein drop 660 and ligand drop 630 may be equal, unequal drop sizes may also be used. The hydrophobic surface of insulating layer 640 minimizes the adhesion of drops 630 and 660 to the surface, which reduces the drag on the drops during merging. In this example, the hydrophobic surface is made of a fluorinated polymer, such as, for example, 3M™ Fluorad™, Dupont Teflon® AF, 3M™ EGC-1700, or plasma-deposited fluorocarbons. In one implementation, a parylene coating may be used as the insulator layer, as well as for the hydrophobic surface.

Alternatively, the thermometer material (e.g. amorphous silicon) itself may be utilized to construct drop mover electrodes. Also, the electrodes and thermometer may be fabricated in different layers, with the electrodes in a layer between the drop deposition points and the thermometer, to enable placing metal drop mover electrodes on top of the thermometers. In this approach, an electrically insulating layer separates the thermometers and electrodes.

The parent application, incorporated herein by reference, describes several available technologies for drop delivery, including syringes and other types of dispensers and techniques such as pin spotting.

Figure 7:
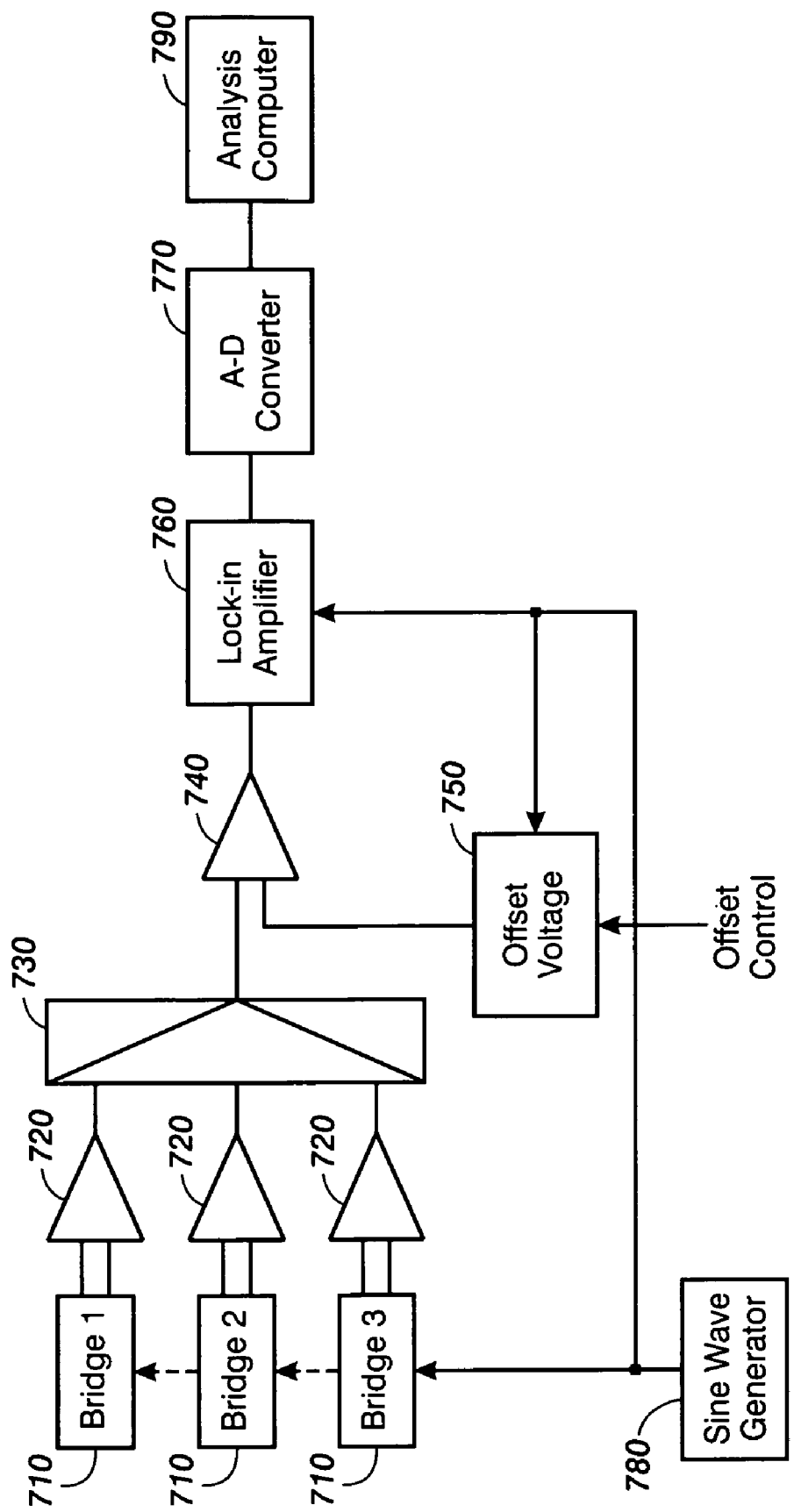
FIG. 7 is a schematic diagram of a second electronic measuring system.

FIG. 7 shows a schematic of a second implementation of an electronic measuring system. For the purposes of example, an alternating current (AC) detection method is illustrated. The AC detection method eliminates the 1/f noise inherent in electronic devices, in which the 1/f noise can be significant at frequencies up to 1 kHz. A bridge circuit is used to detect changes in the resistance of the thermometers. The electronic circuitry implements four functions: amplification of the output of the bridge, zeroing of the bridge, detection of the signal, and computer analysis of the signal. To each bridge 710, a sine wave is provided by generator 780. This sine wave drives the two input terminals of each bridge.

Each bridge has two output terminals whose difference represents the temperature difference of the reference and measurement cells of the bridge. The signal on these two terminals is amplified by a low-noise signal amplifier 720. Because the signal level is low, noise introduced by this function must be minimal, but noise minimization must be balanced by design considerations. For example, for the array to be disposable, which is desirable in some applications, the amplifiers must be located off the array, but amplifiers placed on the periphery result in the introduction of noise through the longer lead length. To minimize noise from interconnect, the amplifiers may be placed on a separate temperature-controlled heat sink positioned in close proximity to the detector array, with amplifiers 720 placed directly above the detector array and contacting the array through compressible pogo-pin connectors. An additional advantage of placing each amplifier directly above its associated bridge is that the bridge output signal wires do not have to pass near any other wires, and thereby avoid noise coupling.

A multiplexer 730 enables several individual detectors to use one lock-in amplifier 760 and analog-to-digital (A-D) converter 770. With the implementation shown in FIG. 7, advantage is derived by the use of one signal amplifier for each detector and placement of multiplexer 730 after the amplifier. The noise introduced by the multiplexer contributes a smaller relative amount than if the multiplexer had been placed before the signal amplifier. Alternatively, if noise levels permit, the multiplexer could be placed before the signal amplifiers, allowing fewer signal amplifiers and a more compact arrangement of amplifiers and bridges.

The temperature sensors in each bridge may be similar but not identical with each other. After temperature equilibration, the output of the bridge will not quite be zero because of these differences. The output will be a small sine wave proportional to the difference. This common mode signal, if not reduced, limits the amount of amplification between the bridge and lock-in amplifier 760. This in turn limits the system sensitivity. The common mode signal is minimized by a bridge zero operation performed after the initial amplification through second stage amplifier 740, which also receives a signal from offset voltage source 750. An offset control signal to source 750 selects a proportion of the sine wave reference signal to be subtracted out of the amplified input signal. This control signal is set by measuring output after equilibration and then setting it to minimize the common mode output. If the inherent balance of the bridge is sufficient, the offset amplifier is not needed.

Lock-in amplifier 760, which produces DC output indicating amplitude of the detector signal, may be implemented with known lock-in amplifiers or equivalent circuitry. Alternatively, the lock-in operation could be implemented in software. In general, a lock-in amplifier can be used to measure signals buried in noise. A lock-in amplifier does this by acting as a narrow bandpass filter that removes much of the unwanted noise while allowing the signal being measured to pass through.

A standard lock-in amplifier known in the art includes a variable gain input amplifier that increases input signal amplitude; a phase detector; and a low-pass filter with adjustable cut-off frequency. The lock-in amplifier receives an input signal with an unknown value and a reference sine wave at the frequency of modulation of the signal being measured. After input amplification, the input signal is mixed with the reference signal (this operation is also known as phase detection) and then sent through the low-pass filter. This low-pass filtering effectively removes substantially all electronic noise that is picked up between the source (in this case, the Wheatstone bridge) and the output. The DC-coupled output signal of the lock-in amplifier is proportional to the amplitude of the input signal.

The analog output of the lock-in operation is digitized by A-D converter 770 (conventionally included within lock-in amplifier 760, providing a digital output signal) and can be input into computer 790 for analysis. Amplitude of the digitized signal represents temperature difference on the bridge. After the drops are moved together and when a reaction occurs, the amplitude will increase until the drops are fully mixed and then decrease as heat is removed through conduction and evaporation. If no reaction occurs, no significant change will occur in the amplitude. The computer can correlate the digitized signal against expected temperature increase and decrease. If the correlation is positive, then the occurrence of a reaction is signaled.

Figure 8:
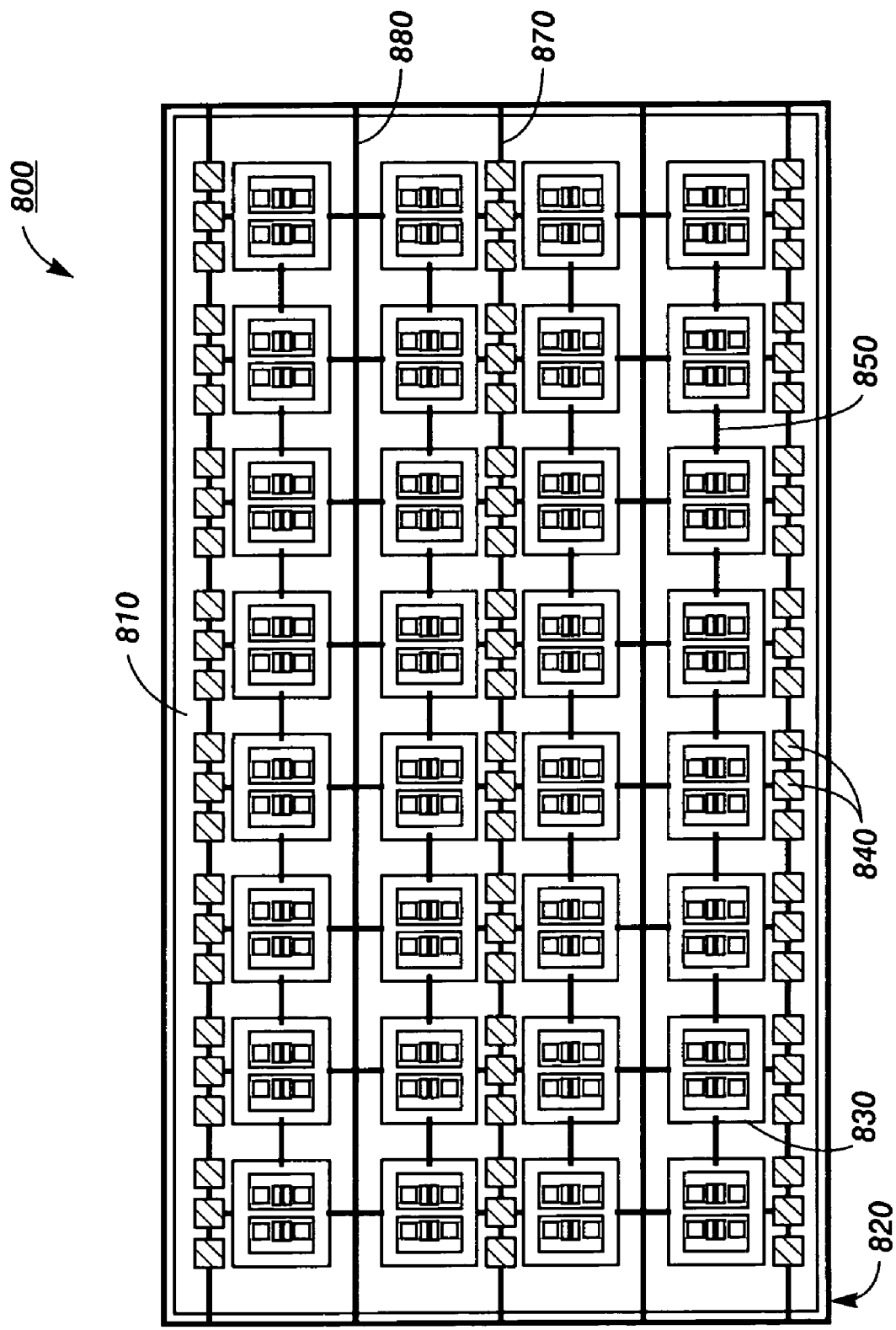
FIG. 8 is a top plan view of an array of components of a nanocalorimeter that can be used with the system of FIG. 7.

FIG. 8 shows detectors of a detector array arranged in a rectilinear orientation to form a matrix array. In this example, the array is fabricated on thin plastic sheet 810, for example a 12-24 µm thick Kapton® plastic substrate, and is supported by heat sink 820, which is made of a material with a high thermal conductivity such as Cu or Al. Thin film conducting lines 850 placed in the regions between individual detectors 830 serve as electrical interconnect that carry signal and power between the detectors and the electronic module on the outside. Detectors 830 require interconnect for signal excitation and drop merging electrodes. All detectors in pairs of adjacent rows are connected to common merge-electrode power 880.

The resistive thermometers, drop merging electrodes, and electrical interconnect may be patterned on one side of the matrix array, and the thermal equilibration film may be fabricated on the other side. Measurements can be made simultaneously in two rows. Detector signal and ground are provided through contact pads located over the heat sink adjacent to each detector and connected to the array through detector amp contact pads 840. Common bridge-excitation is provided for pairs of rows by bridge power conducting lines 870. The merge-electrode power and common bridge-excitation are introduced through alternating rows. Because it is desirable to transfer fluids from standard storage devices, such as well-plates having different densities (96 well, 384 well, or 1536 well) the detectors have the same 9 mm square layout as standard 96 well-plates used in the biotechnology and pharmaceutical industries.

An array like that in FIG. 8 illustrates an example of an array with a support layer and not less than one detector on the support layer. Each detector includes two or more resistive thermometer elements on the support layer, together with bridge circuitry. The bridge circuitry electrically connects first and second subsets of the thermometer elements in a bridge, and the bridge circuitry has one or more detection points. The bridge circuitry is capable of being driven to allow electrical detection, at the detection points, of differences between first and second temperature changes. The first temperature change is received by the first subset of the thermometer elements and the second temperature change is received by the second subset of the thermometer elements.

The above-described techniques for producing the array of FIG. 8 also illustrate an example of a method of producing detectors that includes producing resistive thermometer elements and bridge circuitry as described above. More particularly, the thermometer elements and the bridge circuitry are produced on a support layer.

Figure 9:
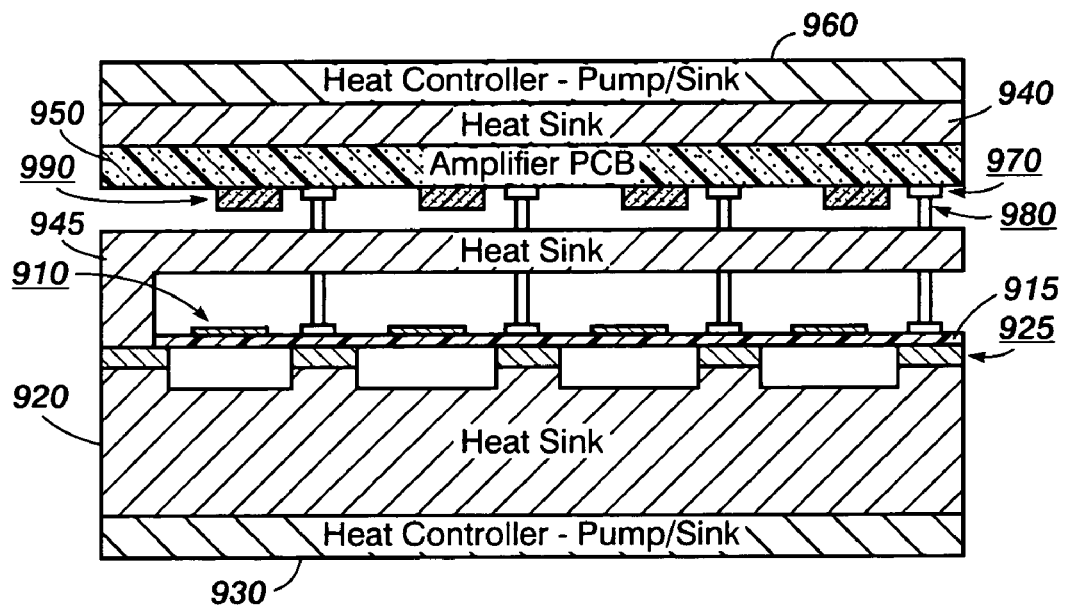
FIG. 9 is a cross-sectional diagram illustrating the operating environment of a nanocalorimeter as in FIG. 8.

FIG. 9 shows a cross-section of the nanocalorimeter assembly and its detector environment, which provides thermal isolation, electrical connections and sample delivery. To achieve thermal isolation, the environment is structured to insure that the heat transferred to or from the drop is minimized to a value as close to zero as possible; one technique employs a cap over a sensing region, as described in relation to FIG. 19 of copending U.S. patent application Ser. No. 11/167,746, entitled "Thermal Sensing" and incorporated herein by reference; another approach is to perform signal processing on resulting data to correct for heat transfer. The three main heat transfer channels for the assembly include: thermal conduction through the air, thermal conduction across the supporting medium, and evaporation, with evaporation being much larger than the others.

To reduce evaporation to acceptable limits, measurements can be conducted at low temperatures and high humidities, for example 5° C. in near 100% relative humidity (e.g. non-condensing). Specifically, evaporation is controlled in part by maintaining near 100% relative humidity, within some acceptable tolerance, of the solvent used to dissolve the chemicals being investigated. This may be accomplished by exposing a reservoir of solvent to the atmosphere in the chamber enclosing the detector. The lower temperature reduces the vapor pressure of the solvent, and higher humidities reduce the concentration gradient of solvent in the gas phase near the surface of the drop, thereby reducing the driving force for evaporation. In other implementations, reasonable measurements might be attainable at higher temperatures or lower humidities despite the correspondingly higher evaporation rates, in which cases operation at low temperatures or high humidities may not be necessary.

Thermal conductivity through the surrounding environment can be reduced through use of a controlled atmosphere, for example an environment rich in xenon or argon, which have lower thermal conductivities than air. Conductivity can also be controlled through the use of a partial or complete vacuum, aerogels or other insulating materials, and other methods that will occur to those skilled in the art.

To minimize thermal conduction across the supporting medium, detector 910 resides on substrate 915, which is supported by substrate carrier 925, which is in contact with heat sink 920. In this example heat sink 920 is comprised of copper, but other materials known in the art could also be utilized. Heat sink 920 may be in thermal contact with an optional active temperature control device 930, which controls the temperature of the heat sink to within 1 mK to 0.1 K of amplifier heat sink 940.

The detector amplifiers dissipate power (10 mW each), which may be too much heat for the detector heat sink in some implementations. The amplifier power can be sunk to a separate heat sink if desired. Signal amplifiers 990 reside on amplifier printed circuit board (PCB) 950, which is in contact with heat sink 940. The temperature of heat sink 940 can be controlled by a temperature control device 960, if desired for a particular implementation. Pogo-pin connectors 980 connect amplifier PCB 950 with detector substrate 915 through amplifier pads 970.

There are several conditions in which the heat sink 920 does not need to be temperature controlled. In these cases, the heat sink is thermally isolated from the enclosing chamber using standard low conduction materials like glass, plastic or stainless steel tubing. In these cases, the amplifier PCB 950 is placed in direct contact with the temperature controlled enclosing chamber.

Tables 3 and 4 and the related description in the parent application, incorporated herein by reference, illustrate the magnitude of temperature fluctuations that heat sink 920 may experience.

Figure 10:
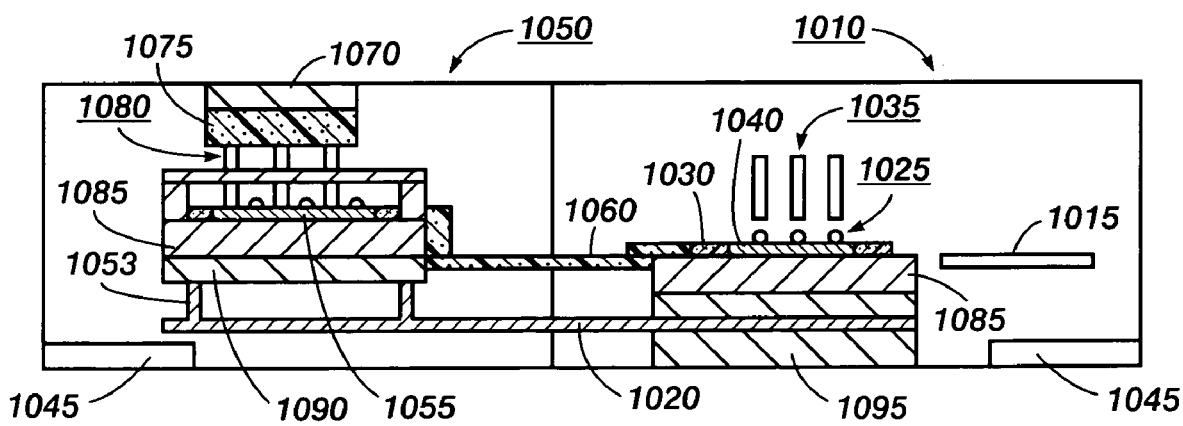
FIG. 10 is a cross-sectional diagram illustrating an implementation of process flow of a nanocalorimeter as in FIG. 8.

FIG. 10 illustrates a cross section of a measurement system utilizing the array described above. The measurement system in this example configuration includes two compartments, load lock chamber 1010 and measurement chamber 1050. The chambers and the atmosphere contained within them are equivalent; they are at the same operating temperature. The atmosphere within each chamber is a non-reactive gas, for example xenon, argon, air, or nitrogen, at a near 100% relative humidity for the solvents used in the drops being measured, and this humidity level is maintained through use of vapor pressure reservoirs 1045. The temperature of the chamber walls is controlled to within 0.1 K. Heat sink 1085, mounted on heat conductor 1090, receives heat from the power dissipated in the measurement thermometers on detector array 1040 when in the measurement chamber 1050. In this example four thermometers are used for each detector, as shown in FIG. 1, and each thermometer dissipates approximately 4 μW. The rate of temperature increase of heat sink 1085 due to thermometer heating is approximately 10 μK during a 10 second measurement, based on a 96 detector array and a heat sink with a heat capacity of 1500 J/K (refer to Table 3 above). Detector array 1040 is connected to detector array electronics 1030 which in turn are connected to system electronics 1060. Biomaterials are contained within a biomaterial storage well plate 1015, which is placed in the load lock chamber 1010. In the measurement chamber 1050 are detector electronics 1075 as well as the associated heat sink/controller 1070 for the detector electronics.

Biomaterials 1025 are deposited on the array with chemical deposition device 1035 in preparation for the measurement. While in the load lock chamber 1010, the heat sink 1085 and associated detector 1040 and biomaterials 1025 are brought into thermal equilibrium with the chamber through heat conductor 1095. Heat conductor 1095 may be any material or system of high thermal conductivity, and may be, for example, a metal block such as copper or aluminum that is in good thermal contact with both the chamber wall and the heat sink 1085. As shown in FIG. 10, thermal contact of heat conductor 1095 with heat sink 1085 occurs through the array transporter 1020. However, this configuration is exemplary only; other configurations will occur to those skilled in the art and are contemplated by the disclosure herein.

In alternative implementations, heat conductor 1095 may have active temperature control, such as control by a circulating-fluid refrigeration or heating system, a Peltier device, a resistive heater, a heat pump, or any of a number of other active temperature-control devices known by those skilled in the art. Furthermore, the heat conductor and associated temperature control function can be integrated into the array transporter 1020. Array transporter 1020 moves a detector array with deposited biomaterials from the load lock into measurement chamber 1050 and, in this example, utilizes a circular motion so that a detector array with measured materials is simultaneously moved from the measurement chamber to the load lock. Other array transport methods may be utilized, such as pick-and-place devices and belt devices with elevators.

Once in the measurement chamber, the detector array is raised into contact with the pogo pins, and simultaneously the heat sink 1085 (with heat conductor 1090) is raised above the transporter 1020 and thermally isolated from it by supporting pins 1053. The supporting pins may be fabricated from any good thermal insulating material with sufficient mechanical strength, such as glass rods, stainless steel hollow tubing, plastic rods, porous ceramics, and other materials known to those skilled in the art. Other configurations are possible; for example, a temperature controller may be used to maintain heat sink 1085 at a specified temperature in measurement chamber 1050, for example within 1 mK of the temperature of heat sink/controller 1070 of detector electronics 1075, rather than relying on thermal isolation alone. Pogo-pin detector connectors 1080 make electrical contact directly to the detectors to transmit thermal change information from the detector array to detector electronics 1075. This type of connector is used in this example to provide a nonpermanent connection that allows connection to be made to successive arrays with low thermal contact to the array and good placement accuracy with a small foot-print that provides symmetrical contact to the measurement and reference regions to enable precise differential measurements.

In operation, detector array 1040 is placed in load lock chamber 1010 while a previously set-up detector array 1055 is being measured in measurement chamber 1050. The initial temperature of detector array 1040 could, for example, be within 1 K of the temperature of load lock chamber 1010, or measurement could be timed to avoid this and other temperature constraints. The proximity of measurement chamber 1050 to load lock chamber 1010 enables the connected detector array to be moved between the chambers while remaining in a controlled environment. Biomaterials are then moved into load lock chamber 1010 and stored in an appropriate vehicle 1015, such as a 384 or 1536 well plate, although other containers or well plate sizes would also be appropriate. Biomaterials 1025 are then deposited on detector array 1040 using, for example, an aspirating/printing system or an automated syringe-type loader 1035. Deposition device 1035 is maintained at a controlled temperature to avoid warming biomaterials 1025. Initially, detector array 1040 is connected to detector array electronics 1030 and system electronics connector 1060, which provides the necessary electrical connections to all the detector elements in detector array 1040 with the exception of the detector electronics for the measurement bridge. Depending on conditions, the detector bridges in detector array 1040 may be driven by the AC sine wave (for example, element 560 in FIG. 5) to self-heat to a temperature that equilibrates the drop temperature with the controlled environment in the load lock chamber. This signal is conducted through the system electronics connector 1060 to the detector array electronics 1030.

After the deposited materials 1025 come to thermal equilibrium with the detector array 1040, the detector array 1040 with deposited chemicals 1025 is then moved from load lock chamber 1010 to measurement chamber 1050 by array transporter 1020 and measured detector array 1055 is moved into load lock chamber 1010. This movement may be accomplished through a rotation, such as a 180-degree rotation, or by any other means known in the art. Within measurement chamber 1050, the detector array is in thermal contact with heat sink 1085, which in this implementation is thermally isolated from transporter 1020 by supporting pins 1053 in measurement chamber 1050. The measurement sequence is initiated by applying the AC sine wave to the detector bridges. This signal is created by an AC generator located on the amplifier PCB 1075 and conducted to detector array 1055 through the pogo pins 1080. The detector bridge is then zeroed by properly setting the offset voltage. Thermal equilibration is confirmed by measuring the voltage across the detector bridge for a short period of time. When the rate of change of this voltage is below a pre-specified level, the system is in thermal equilibrium. The zeroing operation may need to be repeated during this process.

A row of drops of deposited chemicals 1025 is then merged and mixed on the surface of the detector array. This is accomplished by applying a drop moving voltage from the amplifier PCB 1075 through the pogo pins 1080 to the detector array 1055. The transient voltages generated from the merging voltages are allowed to dissipate. The reaction during mixing is then measured by detecting the imbalance in the bridge. Each bridge in the row is measured repeatedly for a period of time and the data is input into the computer for analysis.

Merging drops in this way illustrates an example of a method of using a device as described above. The method includes depositing drops of fluid on a reaction surface and a reference surface. The method also includes simultaneously activating drop merging electrodes in the regions that include the reaction surface and the reference surface to cause simultaneous reactions on the surfaces.

Simultaneous activation of drop merging electrodes is advantageous because it allows minimization of background changes due to changes in drop surface area caused by different evaporation rates or other causes. Background changes can be minimized because the reactions in the measuring region and the reference region are activated simultaneously. In the meantime, appropriate signals can be provided to the bridge circuitry to allow detection of a voltage difference between the detection points. In other words, detection can be an ongoing process that begins before the merging electrodes are activated, with the feedthrough from the drop merge signal available as an indicator that the reaction has begun.

The individual bridges in a single row may be multiplexed in the detection electronics. A measurement is made on one detector and then the next detector in the row until all the detectors in the row have been measured. This is repeated for a period of time until all measurements for the row are complete. Alternatively, multiple instances of the detection electronics can simultaneously measure all the detector arrays in the row. To further reduce measurement time, measurements may be performed in blocks of two or more rows.

FIG. 11 is a schematic diagram of an electronic measuring system similar to that shown in FIG. 5, but with different details. Measuring system 1100 includes thermistor bridge 1102, instrumentation amplifier 1104, and lock-in amplifier 1106.

The term "thermal input signal" refers herein to a signal provided to a component in the form of thermal change, and the thermistors in thermistor bridge 1102 receive different thermal input signals. Thermistor bridge 1102 includes two pairs of opposite thermistors, arranged in a Wheatstone bridge that suppresses, to the first order, common-mode variations, i.e. variations in output signal as a result of common variations, i.e., variations in output signal as a result of common variations in resistance of all the thermistors. Implementations of low noise thermistors and related techniques are described in greater detail in co-pending U.S. patent application Ser. No. 11/167,748, entitled "Resistive Sensing" and incorporated herein by reference in its entirety.

Thermistors 1110, referred to as "measuring thermistors," are located so that they are exposed to a thermal input signal that is being measured, while thermistors 1112, referred to as "reference thermistors," are located to make a reference measurement. For example, if the thermal effect of a reaction is being measured, thermistors 1110 can be located so that a thermal signal indicating heat from the reaction would be conducted or otherwise provided to them, while thermistors 1112 can be located away from and insulated from the reaction so that they receive no such thermal signal.

Instrumentation amplifier 1104 amplifies the difference voltage between nodes 1114 and 1116 of bridge 1102 and can be implemented as a low-noise, very high impedance amplifier. Its output is provided to lock-in amplifier 1106, which performs second stage amplification, removing additive voltage noise by bandwidth narrowing. The voltage VB provided to bridge 1102 is a sinusoidal voltage derived from the internal reference voltage source 1120 of lock-in amplifier 1106. Lock-in amplifier 1106 also includes an amplifying component 1122 that receives the reference voltage and the output from instrumentation amplifier 1104 and provides the output signal $V_{out}$. $V_{out}$ is proportional to the difference between the temperature sensed by the measuring thermistors 1110 and the temperature sensed by the reference thermistors 1112.

The circuitry in FIG. 11 can generally be implemented with standard electrical components, except that bridge 1102 includes thermistors with particular noise properties under a device's operating conditions. For example, they can be low noise thermistors or they can be thermistors that include materials with specific noise characteristics. In a low noise implementation, instrumentation amplifier 1104 and other resistors (not shown) would also be selected for low noise characteristics under the device's operating conditions. The term "operating conditions" is used herein to refer to the relevant conditions under which a calorimeter or other thermal sensing device is designed to operate, such as dissipated power, bias voltage, ambient temperature, and so forth.

As used herein, a "low noise thermal sensor" is a thermal sensor for which the noise equivalent temperature difference (NETD) is not greater than approximately 50 µK over a typical thermal sensing bandwidth range of approximately 3 Hz or more under a device's operating conditions; a typical thermal sensing bandwidth range is 0.1 Hz to 4.2 Hz, for example, and a bandwidth range of 1 Hz to 4.2 Hz is also useful in some situations. NETD of a thermal sensor refers herein to the apparent temperature difference between an object and its surroundings that produces an effect equal to the intrinsic noise of the sensor; it could also be described as the differential temperature at which the signal to noise ratio of the sensor is unity. A "low noise thermistor" is accordingly a thermistor that can be used in a low noise thermal sensor.

Also, a thermistor that does not fall precisely within the above definition of a low noise thermistor could be advantageously used in bridge 1102. For example, if bridge 1102 includes thermistors with vanadium oxide ($VO_x$) deposited at room temperature, bridge 1102 can easily have NETD not greater than approximately 100 µK over a thermal sensing bandwidth range of approximately 3 Hz or more under a calorimeter's operating conditions; as described in greater detail below, $VO_x$ thermistors have been fabricated and included in thermal sensors with NETD not greater than approximately 35 µK or even 10 µK over a bandwidth range of 1 Hz to 4.2 Hz under appropriate operating conditions. This is advantageous because deposition of $VO_x$ at room temperature is consistent with fabrication on substrates such as polyimide, which is not readily compatible with the temperatures necessary for PECVD deposition of amorphous silicon, a frequently used thermistor material.

In general, resolution of a temperature measurement made by system 1100 in FIG. 11 is limited by several factors: Thermistor noise; contact noise, such as from pogo pin contacts or other contacts; other electrical noise, such as from the amplifiers; TCR of each thermistor; maximum bridge supply voltage $V_B$ allowed; and limits in the common-mode rejection ratio of the Wheatstone bridge. By performing a noise analysis on an implementation of system 1100, it is possible to optimize electrical components for noise. For example, lock-in amplifier 1106, with a reference frequency typically around 1000 Hz, suppresses most of the 1/f (low frequency) noise originating from the electronics itself or the environment.

The amplifier portion of system 1100 can also be empirically calibrated by connecting it to dummy metal film resistor bridges, in which case the measured noise lies close to the theoretical Johnson noise, also known as thermal noise, i.e. the theoretical minimum achievable noise level; specifically, the measured noise in such a setup is typically a factor of 2 greater than the theoretical Johnson noise. Actual measurements of contact noise from pogo pin contacts indicate that this noise does not play a significant role at current noise levels, though it might if even lower noise levels can be achieved. Maximum bridge supply voltage $V_B$ is limited by self-heating and by the input range of instrumentation amplifier 1104. More specifically, offset arises because the thermistors in bridge 1102 are not ideally matched, and the offset causes limited common-mode rejection through differential self-heating, as well as causing amplifier input range limitations. Small thermal imbalances and fluctuations between measuring thermistors 1110 and reference thermistors 1112 also limit common-mode rejection and measurement resolution because they result in erroneous signals.

After optimizing other components for noise, it is still possible to obtain further improvement by optimizing thermistors 1110 and 1112, both for noise and for TCR. Both noise and TCR of the thermistor material affect the NETD of the thermal sensor, which is used as a figure of merit for the sensor. Assuming that a thermistor's resistance is a linear function of temperature, which is a valid approximation for small temperature variations, and that the four resistors in the Wheatstone bridge are well-matched, the NETD of bridge 1102 can be calculated as follows:

$$NETD = \frac{2 \cdot V_{noise}}{V_{bridge} \cdot TCR} \quad \text{(Eq. 1)}$$

where $V_{bridge}=V_B$ in the implementation of FIG. 11 and $V_{noise}$ is an observed noise voltage at nodes 1114 and 1116.

FIG. 12 shows a top plan view of a pair of thermistors 1140 that can be used in bridge 1102 in FIG. 11, either thermistors 1110 or thermistors 1112. Each thermistor includes a rectangular slab of thermistor material, with slab 1142 being on the left in FIG. 12 and slab 1144 on the right. Each slab has dimensions W and L, which are illustratively shown for slab 1142, and the dimensions of slab 1144 are substantially identical. Leads 1150 and 1152 have interdigitated lines that extend across slab 1142, while leads 1154 and 1156 have interdigitated lines that extend across slab 1144. On the opposite side of layer 1162 from slabs 1142 and 1144 is thermally conductive component 1160, which extends to an adjacent region at which it is exposed to the temperature either of a reaction or a reference. When the reaction occurs within a fluid drop under control of drop merging electrodes, component 1160 thermally couples the drop with slabs 1142 and 1144, providing a thermally conductive path from the drop to thermal sensors that include slabs 1142 and 1144.

Figure 13:
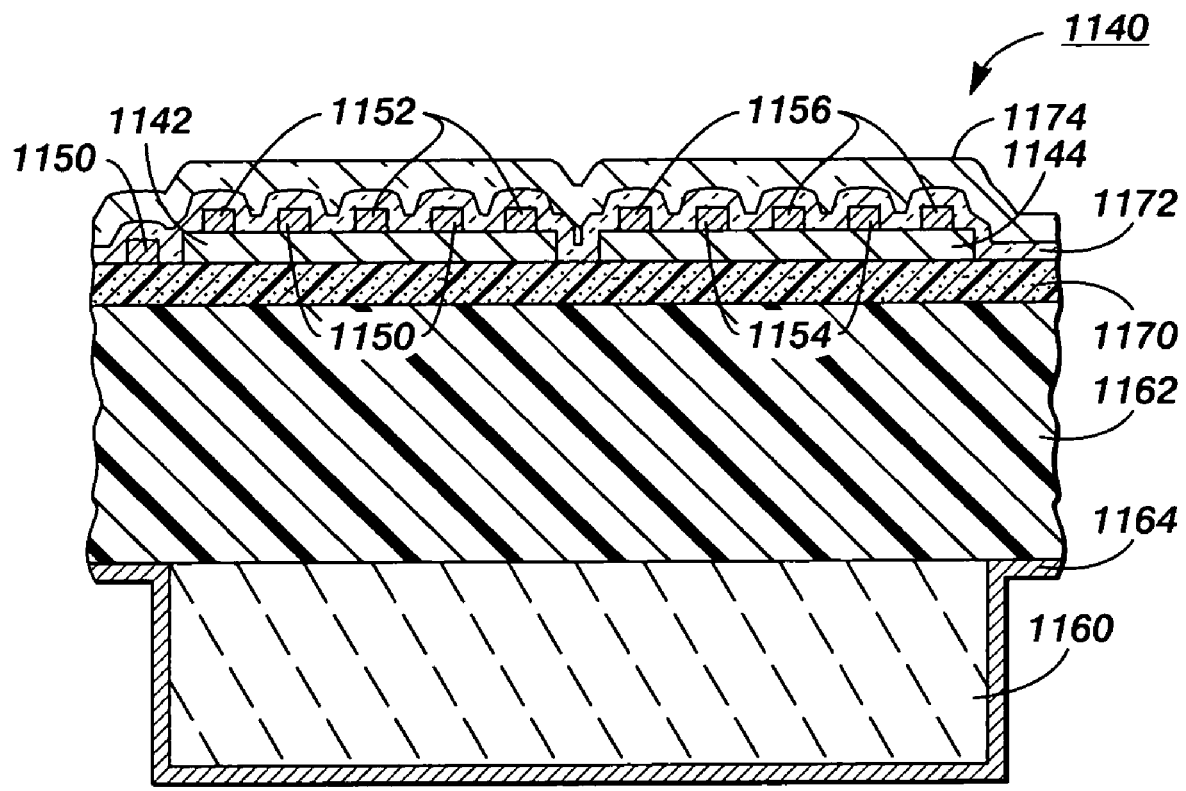
FIG. 13 is a cross section of the pair of thermal sensors, taken along line 13-13 in FIG. 12.

FIG. 13 shows thermistor pair 1140 in cross-section along the line 13-13 in FIG. 12. Polymer layer 1162 can, for example, be a 1 mil (25.4 µm) thick polyimide layer, such as Kapton® film from DuPont, on which other components are microfabricated in a manner described in greater detail below in relation to FIG. 15. Polymer layer 1162 provides thermal isolation between thermistor pair 1140 and other components, and, for this purpose, any other suitable thermally isolating film could be used instead of polymer, including inorganic materials.

Thermally conductive component 1160 is on the lower surface of polymer layer 1162, and can include thermally conductive metal such as copper or aluminum at a thickness of 9 µm or thinner; in general, component 1160 can include any thermally conductive material and desired conduction can be obtained by adjusting thickness in proportion to the material's thermal conductivity.

Deposited over thermally conductive component 1160 is anti-coupling layer 1164, which could be implemented as a 10 nm thick layer of gold, and functions to prevent capacitive coupling between adjacent parts of thermally conductive component 1160; because it is very thin, layer 1164 has low thermal conductivity, preserving thermal isolation. Layer 1164 is believed to reduce noise by coupling component 1160 to ground, preventing slabs 1142 and 1144 from capacitively accumulating additional charge that could affect their response to thermal input signals. Implementations of layer 1164 and of other applicable anti-coupling measures are described in greater detail in co-pending U.S. patent application Ser. No. 11/167,746, entitled "Thermal Sensing" and incorporated herein by reference in its entirety.

On the upper side of polymer layer 1162, barrier layer 1170 protects against contaminants and humidity, increasing device performance; barrier layer 1170 has been successfully implemented with a layer of approximately 300 nm of silicon oxynitride ($SiO_xN_y$). Slabs 1142 and 1144 are on barrier layer 1170, and include material making it possible for thermistor pair 1140 to be low noise thermistors. Leads 1150, 1152, 1154 and 1156 are on slabs 1142 and 1144 and, in places, on barrier layer 1170; leads 1150 can be implemented, for example, with a suitable conductive metal sandwich such as Cr/Al/Cr or TiW/Al/Cr to provide electrical contact with slabs 1142 and 1144 and to provide conductive paths to other circuitry discussed in greater detail below.

Additional layers deposited over leads 1150, 1152, 1154, and 1156 provide electrical passivation, environmental barriers, and hydrophobic surfaces, which are especially useful for a system in which temperature of reactions between fluids are measured through drop deposition and merging. In FIG. 13, these layers illustratively include protective layer 1172 and polymer layer 1174. Protective layer 1172 can be produced by plasma-enhanced chemical vapor deposition (PECVD) of silicon oxynitride, while polymer layer 1174 can include a layer of parylene to provide a barrier to liquid and to electrical leakage and to provide some hydrophobicity. Fluorocarbon polymer can be dip coated over the parylene to obtain a more hydrophobic surface. Alternatively, polymer layer 1174 could include a Teflon® coating from DuPont or a similar material.

Figure 14:
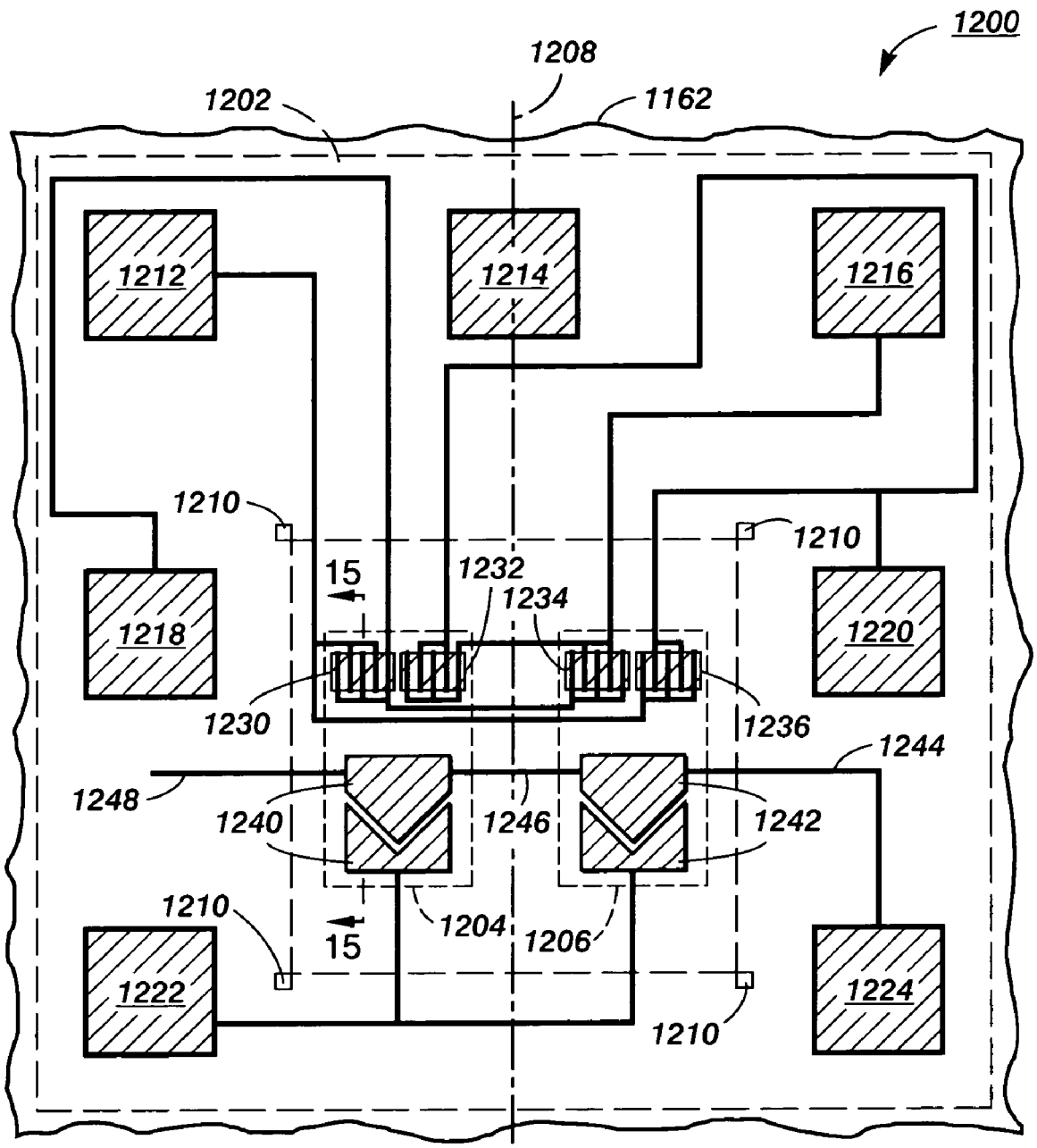
FIG. 14 is a partially schematic top view of a thermal sensing cell that includes two pairs of thermal sensors like those of FIGS. 12 and 13.

FIG. 14 illustrates a thermal sensing cell 1200 that includes two pairs of thermal sensors like those shown in FIGS. 12 and 13. Frame 1202 (shown in dashed lines) supports polymer layer 1162 (FIG. 13) from underneath. In addition, islands 1204 and 1206 (shown in dashed lines) are on the underside of polymer layer 1162 and each can be implemented like thermally conductive component 1160 (FIG. 12). As described in more detail below, these and other components of cell 1200 are generally symmetrical about axis of symmetry 1208, with the left and right sides of the cell being nearly mirror images of each other. Axis 1208 is approximately straight and extends across polymer layer 1162.

Frame 1202 illustratively has alignment structures 1210 at the corners of a recess within which islands 1204 and 1206 are positioned. Frame 1202 can, for example, be formed from 1 mm thick stainless steel in which alignment structures 1210 and the recess for islands 1204 and 1206 are etched, and the recess can then provide thermal isolation between islands 1204 and 1206 as well as between either of the islands and frame 1202. Thermal isolation could be maintained in various other ways.

Contact pads 1212, 1214, 1216, 1218, 1220, 1222, and 1224 are on the upper surface of polymer layer 1162 over frame 1202. Each contact pad (except contact pad 1214) is connected to one or more of the components over islands 1204 and 1206 by leads that are shown schematically in FIG. 14. If cell 1200 is approximately square with 9 mm sides, the contact pads can be approximately 1 mm×1 mm, allowing connection with pogo pins. The leads can be approximately 50 µm wide or even wider as long as they do not result in loss of thermal isolation.

Thermistor slabs 1230, 1232, 1234, and 1236 can each be implemented as described above for thermistor slabs 1142 and 1144 (FIGS. 12 and 13), providing two thermistor pairs, one with slabs 1230 and 1232 and the other with slabs 1234 and 1236. The contact pads could be connected in various ways to provide an implementation of bridge 1102. For example, voltage $V_B$ can be applied to one of contact pads 1212 and 1216 while the other is connected to ground to provide a Wheatstone bridge with contact pad 1218 connected to one of nodes 1114 and 1116 and with contact pad 1220 connected to the other. Therefore, one of the thermistor pairs includes measuring thermistors 1110 while the other includes reference thermistors 1112, as can be understood by comparing with bridge 1102 in FIG. 11.

The contact pads in FIG. 14 can be electrically contacted with any suitable connectors such as pogo pins, both for controlling drop merger electrodes and for electrically detecting thermal signals in the bridge. With a polymer layer substrate, crossing lines and vias are problematic. The layout in FIG. 14 provides a simpler layout with no crossing lines and with no vias, in part because all circuitry is within the cell's region, and none of the circuitry extends or connects electrically outside the cell's region except through contact pads. This technique also avoids long, unreliable lines that, if broken, could disable an entire row or column of an array.

FIG. 14 also shows drop mergers 1240 and 1242, on one of which a reaction can be caused and differential temperature measurement performed. Drop mergers 1240 and 1242 illustratively have chevron shaped features, but could also be implemented by any of the techniques described in co-pending U.S. patent application Ser. No. 11/018,757 entitled "Apparatus and Method for Improved Electrostatic Drop Merging and Mixing", incorporated by reference herein in its entirety. Conductive line 1244 extends from pad 1224 to the upper part of drop merger 1242, conductive line 1246 extends between the upper parts of drop mergers 1240 and 1242, and conductive line 1248 extends leftward from the upper part of drop merger to provide some symmetry with conductive line 1244. Pad 1222 is connected to the lower parts of both drop mergers by another conductive line. The conductive lines connected to drop mergers 1240 and 1242 thus illustrate an example of reaction control lines connected to drop merging electrodes in two regions, connected so that the drop merging electrodes are simultaneously activated. Description of features shown in FIG. 14 that relate to providing signals through contact pads and electrical detection through contact pads are described in co-pending U.S. patent application Ser. No. 11/167,635, entitled "Thermal Sensing" and incorporated herein by reference in its entirety.

If a Wheatstone bridge like bridge 1102 is fabricated with elements that are not identical, the bridge has a non-zero "offset voltage" or is "unbalanced", meaning voltage measured across the bridge when temperatures of all thermal sensors are equal; offset voltage can have zero frequency (DC) and non-zero frequency (AC) components. If the bridge's offset voltage is sufficiently great, additional circuitry may be necessary to perform offset voltage correction. The need for additional circuitry depends, of course, on the application, including the range of amplitude of the signals being detected and the sensitivity of circuitry that detects voltage across the bridge. In other words, an application of a bridge as described above has a "sensitivity limit", meaning the amplitude of the bridge's offset voltage that would interfere with accurate detection of the signal being detected; an offset voltage above the sensitivity limit would cause loss of information from the input signal, information whose detection is necessary for the application to satisfy the relevant performance criteria.

Although it is not possible in practice to produce a bridge with four identical elements, the components of the four elements can be shaped and positioned so that offset voltage is below the sensitivity limit for the application despite process variations in patterning layers of material. As used herein, the term "process variations" includes not only variations such as lateral or rotational movements of masks but also different rates of etching in different directions and other variations during fabrication that can result in difference between a finished pattern and its design.

As will be understood more fully from the description of FIG. 15 below, thermistor slabs 1230, 1232, 1234, and 1236 are patterned from a layer of semiconductor material. Part of the bridge circuitry, on the other hand, is patterned from a layer of conductive material such as metal or heavily doped semiconductor material; components patterned from this layer include interdigitated conductive lines that extend across and electrically contact upper surfaces of the slabs and conductive leads that connect the interdigitated lines to each other and to contact pads 1212, 1216, 1218, and 1220.

FIG. 14 illustrates several examples of how components can be shaped and positioned to keep offset voltage below a sensitivity limit despite process variations: Slabs 1230, 1232, 1234, and 1236, for example, have "overlay symmetry", meaning that one could pick up one pair and put it on the other without changing orientation and the two would be virtually identical; as a result, a shift of a mask during patterning of the semiconductor layer would not cause a difference in slab shape. Similarly, interdigitated conductive lines are all parallel to axis 1208, so that they are also tolerant of lateral mask shifts. Also, lines and semiconductor slabs overlap sufficiently that expected misalignment would not result in a short, an open, or another electrical change such as changed resistance; examples of overlap can be seen in both of FIGS. 12 and 14, where each interdigitated line extends beyond and overlaps the upper and lower sides of the slab it contacts and each slab extends beyond and overlaps the outer boundaries of the leftmost and rightmost interdigitated lines that contact it.

Furthermore, left-right symmetry about axis 1208 is another example of shaping and positioning components so that bridge offset voltage is below a sensitivity limit. In addition to the left-right symmetry of thermal sensors, thermally conductive components, drop mergers, and contact pads, the implementation of FIG. 14 illustrates a substantial degree of left-right symmetry in conductive lines and leads, made possible by the left-right symmetry of other components.

As shown, the rectangular slabs are left-right symmetrical with their lengthwise dimensions all aligned and with their widths all contained within a transverse strip extending substantially perpendicular to and across axis 1208. This allows left-right symmetry of the interdigitated lines extending across the slabs. Nevertheless, it has not proved feasible to symmetrically lay out all the transverse leads, i.e. leads that extend substantially parallel to the transverse strip and connect to the interdigitated lines. In the implementation of FIG. 14, none of the transverse leads can be characterized as completely left-right symmetric.

Although not readily apparent in FIG. 14, it is also important that variations in thickness of the slabs be minimized. For example, to achieve thermistor resistances that differ by no more than 0.1%, the thicknesses of the slabs need to differ by no more than 0.1%. For a slab thickness of 300 nm, the difference must therefore not exceed 0.3 nm, an accuracy on the order of a few atom layers of material. Therefore, the thickness of the layer of material from which the slabs are formed must be produced with very high accuracy.

The features described above tend to minimize DC offset voltage resulting from shape and position differences of components within different bridge elements. Sometimes however, AC offset voltage can arise due to capacitive effects.

Also, connecting conductive leads are positioned relative to slabs such that a movement of the mask for one or both of the layers has approximately the same effect on relative position of slabs and conductive leads. As a result, capacitive interactions between slabs and conductive leads remain approximately equal among the bridge elements. This and similar features tend to minimize AC offset voltage resulting from different spacings and other positioning differences between components within bridge elements.

The implementation in FIGS. 12-14 illustrates an example of a device in which first and second subsets of thermometer elements are on left and right sides, respectively, of a symmetry axis extending across a support layer between two regions. The first and second subsets are substantially symmetrical with respect to each other about the symmetry axis. In addition, the device includes first and second thermally conductive structures having thermal contact with the first and second subsets of thermometer elements, respectively, and the thermally conductive structures are also on the left and right sides of the symmetry axis and are substantially symmetrical with respect to each other about the symmetry axis.

The implementation of FIGS. 12-14 also illustrates an example of left and right sets of resistive thermal sensors that are substantially symmetrical about a symmetry axis and that are within a layered structure at one surface of a support structure. On the same surface are left and right input elements that receive thermal input and are also substantially symmetrical about the symmetry axis. The same structure also includes connection elements that electrically connect the thermal sensors in a bridge. On the opposite surface of the support structure is another layered structure that includes left and right components, each with a thermally conductive path extending between opposite the respective input element and opposite the respective set of thermal sensors. The left and right components are also substantially symmetrical with respect to each other about the symmetry axis.

Figure 15:
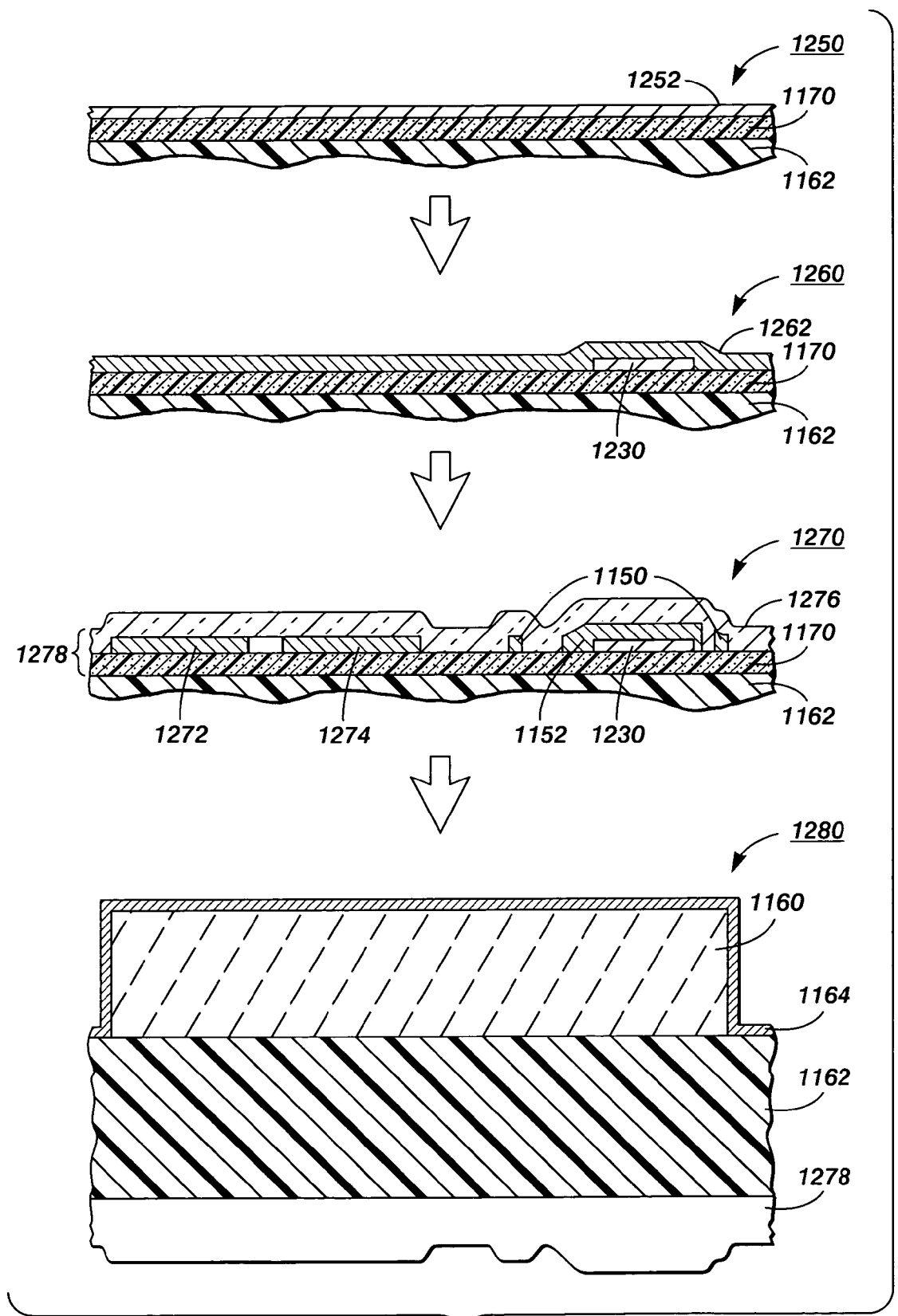
FIG. 15 shows a sequence of cross-sectional views in production of a thermal sensing cell, taken along line 15-15 in FIGS. 12 and 14.

FIG. 15 shows several cross-sections in producing thermal sensing cell 1200, taken along line 15-15 in FIGS. 12 and 14. As can be seen from FIG. 12, line 15-15 extends through the middle digit of lead 1152 where it extends over slab 1142. The operations illustrated in FIG. 15 are similar to those described in Torres, F. E., Kuhn, P., De Bruyker, D., Bell, A. G., Wolkin, M. V., Peeters, E., Williamson, J. R., Anderson, G. B., Schmitz, G. P., Recht, M. I., Schweizer, S., Scott, L. G., Ho, J. H., Elrod, S. A., Schultz, P. G., Lerner, R. A., and Bruce, R. H., "Enthalpy arrays", *Proceedings of the National Academy of Sciences*, Vol. 101, No. 26, Jun. 29, 2004, pp. 9517-9522 ("the Torres et al. article"), incorporated herein by reference in its entirety.

Prior to cross-section 1250 in FIG. 15, polymer layer 1162 is prepared for subsequent operations. As noted above, polymer layer 1162 can be a 1 mil (25.4 µm) or ½ mil (12.7 µm) thick Kapton® film or other polyimide film and is generally held flat during processing, because flatness is important for photolithography and for uniform feature sizes. Prior to deposition of material on polymer layer 1162, the surfaces of layer 1162 are cleaned, and layer 1162 is stretched and mounted by lamination on a frame (not shown). Mounting layer 1162 on a stainless steel frame prevents it from curling or cracking during processing.

Cross-section 1250 shows a portion of polymer layer 1162 on which barrier layer 1170 has been deposited. Barrier layer 1170 has been successfully implemented with a PECVD silicon oxynitride deposited to a thickness of 300 nm, which has been successful in producing a low noise thermistor; other materials may also be suitable, including insulating films such as sputtered $SiO_2$ or PECVD SiO or SiN. When properly deposited, barrier layer 1170 provides improved surface smoothness and a humidity and contamination barrier.

Cross-section 1250 also shows layer 1252 with semiconductor material deposited over barrier layer 1170. Layer 1252 could include vanadium oxide ($VO_x$), heavily p-doped amorphous silicon, or other material suitable for low noise thermistors. Layer 1252 has been successfully implemented by sputtering $VO_x$ over barrier layer 1170 under deposition conditions that obtain required electrical and thermal characteristics and low compressive stress to prevent deformation and provide flatness in layer 1162.

After layer 1252 has been deposited, an annealing operation improves low noise characteristics. In particular, annealing in an appropriate gas such as $N_2$ at a suitable temperature for an appropriate period of time decreases resistivity of layer 1252 and reduces 1/f noise level of a resulting thermistor. Sheet resistance values on the order of 400 KΩ/square have been obtained for a 300 nm thick film of $VO_x$.

Additional information about techniques for producing layer 1252 and about its characteristics and characteristics of other semiconductor layers for low noise thermal sensors is set forth in co-pending U.S. patent application Ser. No. 11/167,748, entitled "Resistive Thermal Sensing" and incorporated herein by reference in its entirety.

Cross-section 1260 illustrates a subsequent stage in which layer 1252 has been patterned, such as by photolithographically producing an appropriate mask and then selectively removing layer 1252, leaving slab 1230 as well as other components such as slabs 1232, 1234, and 1236 (FIG. 14). Any suitable technique could be used, including wet etching, dry etching, or lift-off techniques. After patterning of layer 1252, conductive layer 1262 is deposited, such as by depositing a sandwich of Cr/Al/Cr or TiW/Al/Cr. If layer 1252 includes $VO_x$, TiW/Al/Cr may provide better ohmic contact with $VO_x$, improving noise performance. Lines, leads, and contact pads as shown in FIGS. 12 and 14, when implemented with materials such as these, can provide "low noise output circuitry", a term used herein to refer to circuitry that, if connected to one or more low noise thermal sensors such as low noise thermistors, provides an electrical output signal that includes no more than approximately twice the noise from the low noise thermal sensors. In other words, low noise output circuitry would contribute no more noise than would come from low noise thermal sensors to which it is connected.

Cross-section 1270 shows a subsequent stage at which layer 1262 has been patterned, such as by photolithographically producing a mask and performing selective removal as described above. After patterning of layer 1262, leads 1150 and 1152 extend across slab 1230 as well as around it, while merger portions 1272 and 1274 of drop merger 1240 are also produced. Other leads shown in FIG. 14 are also produced in this stage, as well as the contact pads, all of which include conductive material from layer 1262.

Then, top layer 1276 is deposited, such as by depositing protective layers 1172 and 1174 (FIG. 13). As described above, layer 1172 provides an upper barrier layer. Openings to expose contact pads can be etched through layer 1172, and a thin layer of TiAu or CrAu can then be sputtered and patterned with the same mask, such as by a lift-off process, to provide improved ohmic contact on the surfaces of the contact pads. On top of layer 1172, polymer layer 1174 is deposited, providing an additional barrier and a hydrophobic surface. Openings can then be etched through layer 1174 to expose the thin layer of TiAu or CrAu on the contact pads. The entire structure on the surface of polymer layer 1162 as shown in cross-section 1270 can be referred to as sensor structure 1278.

Cross-section 1280 shows the other side of polymer layer 1162 on which thermally conductive component 1160 has been formed. Cross-section 1280 also illustrates the relationship of component 1160 to sensor structure 1278, shown in profile on the other side of polymer layer 1162.

Component 1160 has been produced by depositing a 9 µm layer of copper, and then patterning it, such as by photolithographically forming a mask and performing selective removal as described above, producing thermally conductive component 1160. In one implementation of this technique, the starting substrate is a pre-manufactured structure that includes polymer layer 1162 on which a layer of copper has been electrodeposited, such as by depositing one or more thin seed layers such as a chromium seed layer and a copper seed layer and then electroplating copper onto the seed layers; in this implementation, the layer of copper can be selectively removed at any appropriate point in the process to produce component 1160. Techniques for producing such a starting substrate are described in U.S. Pat. No. 4,863,808, incorporated herein by reference.

Anti-coupling coating 1164 is then deposited over component 1160. The need for anti-coupling coating 1164 may be reduced or eliminated, however, by using a pre-manufactured starting substrate as described above. More specifically, it may be possible to selectively remove an electroplated copper layer and leave one or more seed layers intact, in which case the remaining seed layers may prevent capacitive coupling and the resulting noise. In general, applicable anti-coupling measures are described in greater detail in co-pending U.S. patent application Ser. No. 11/167,746, entitled "Thermal Sensing" and incorporated herein by reference in its entirety.

After deposition of coating 1164, the resulting structure can be cut off of the frame on which it was mounted during processing and can be attached to frame 1202 (FIG. 14). Frame 1202 acts as a stiffener to hold layer 1162 taut and flat. Further operations can be performed, such as laser trimming of slabs 1142 and 1144 to balance bridge 1102.

When connected in circuit 1100 (FIG. 11), cell 1200 can be operated as follows: Two drops of approximately 250 nl can be released on each of drop mergers 1240 and 1242. The drops on one merger can initiate a reaction such as a protein-ligand binding reaction, an enzymatic reaction, or an organelle activity, while the drops on the other merger can be non-reactive, providing a reference for differential measurement. After the drops reach thermal equilibrium, the drops on both mergers can be concurrently merged and mixed by applying appropriate voltage signals across contact pads 1222 and 1224, as described in the Torres et al. article, incorporated by reference above.

A thermal input signal resulting from merging and mixing of drops is conducted downward through sensor structure 1278 and part of layer 1162 to thermally conductive component 1160. Then, the thermal input signal is conducted laterally through component 1160 to the regions under slabs 1230 and 1232, where they are conducted upward to slabs 1230 and 1232 through part of layer 1162 and layer 1170. A change in temperature in the slabs on one side of cell 1200 changes their resistance, resulting in detection of current through measuring thermistors 1110. The current's magnitude indicates the temperature difference between measuring thermistors 1110 and reference thermistors 1112.

Figure 16:
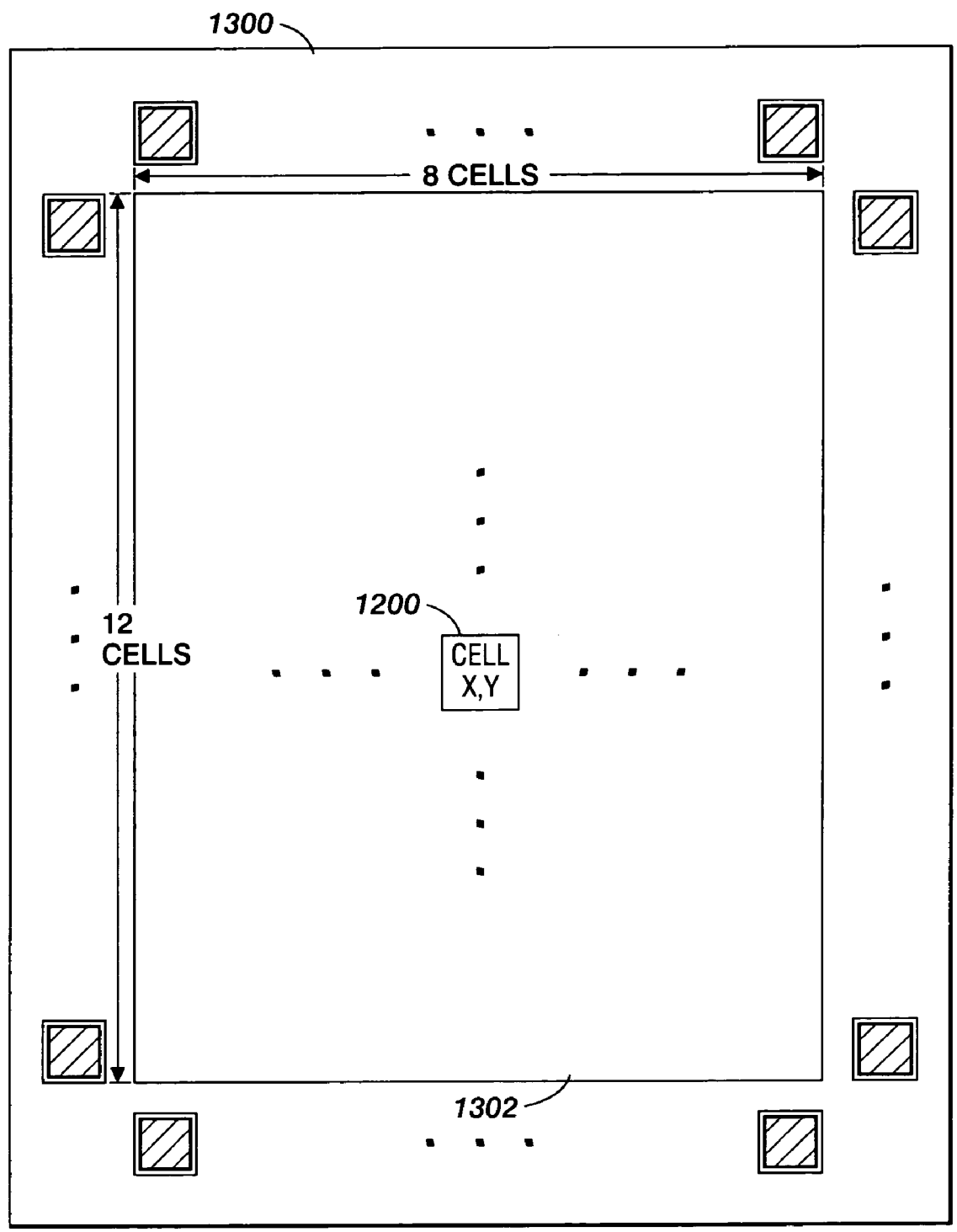
FIG. 16 is a schematic layout diagram of an integrated circuit that includes an array of thermal sensing cells like that shown in FIG. 14.

FIG. 16 shows how an array of cells similar to cell 1200 (FIG. 14) can be integrated on substrate 1300. As shown, array 1302 is 8 cells wide by 12 cells long. To interface with standard automated laboratory equipment, the cells are positioned on 9 mm centers and the automated laboratory equipment connects with the contact pads of each cell as described above. Array 1302 can be one of several arrays fabricated on a single substrate. Features of arrays and cells are also described in co-pending U.S. patent application Ser. No. 11/167,634, entitled "Thermal Sensing" and incorporated herein by reference in its entirety.

The implementations of FIGS. 12-16 include many features that are merely illustrative and could be modified within the scope of the invention. For example, features could be included as described in the Torres et al. article, incorporated by reference above.

Figure 19:
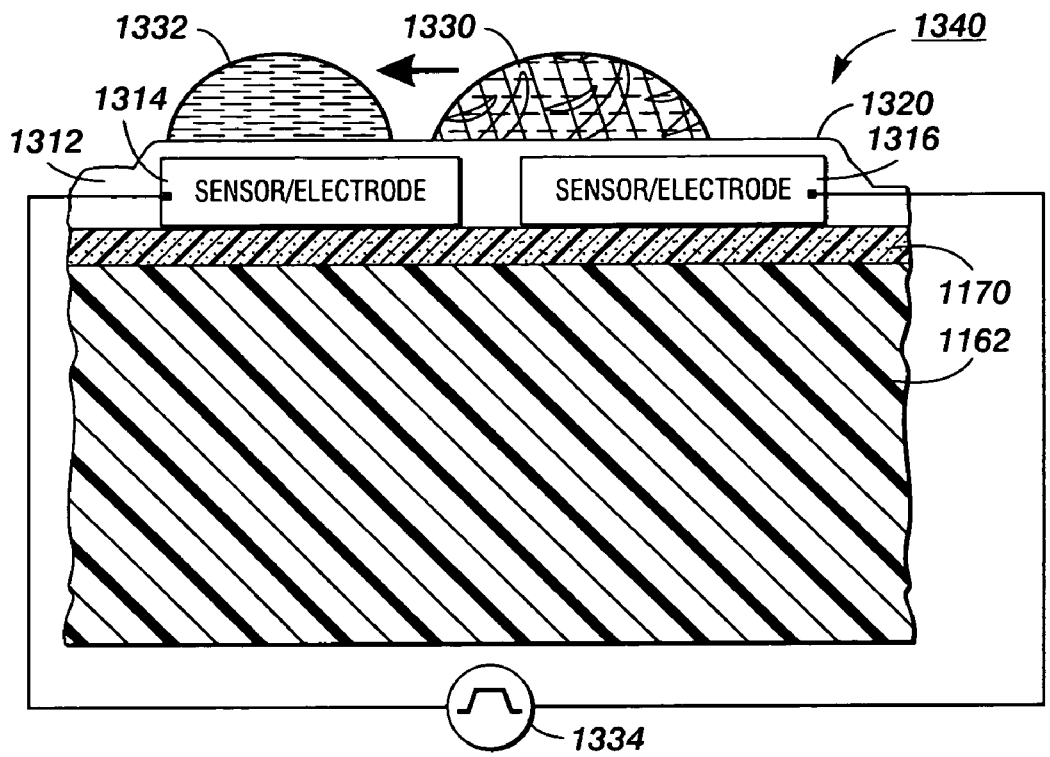
FIG. 19 is a cross section as in FIG. 18 for an implementation without a thermally conductive component.

FIGS. 17-19 illustrate three modifications that could be made to the implementations of FIGS. 12-16, in each case resulting in a cell structure that could be used in the array of FIG. 16. Components that are the same or have similar function as in FIG. 13 are labeled with the same reference numerals.

In FIG. 17, the layer of conductive material that includes lines 1150, 1152, 1154, and 1156 has been deposited and patterned before the layer of semiconductor material that includes slabs 1142 and 1144. This variation is advantageous, for example, if fabrication is divided between two entities, because it addresses a division of labor problem. More specifically, problems arise if one entity is required to work outside its range of expertise or if a workpiece must be handed back and forth between the entities more than once. In the implementation of FIG. 17, one entity could fabricate a preliminary set of components not including the semiconductor layer; after handoff, another entity with expertise in semiconductor processing could then deposit and pattern the semiconductor layer and then deposit one or more additional layers over the components in the semiconductor layer to produce the finished product. Such an approach can be advantageous, for example, where the deposition or patterning of the semiconductor layer requires specialized expertise that is not required for the conductive lines and other components on polymer layer 1162.

Problems arise, however, in the variation of FIG. 17, because of poor electrical contact between slabs 1142 and 1144 and lines 1150, 1152, 1154, and 1156. These electrical contact problems may be caused by one or more oxides formed on the metal conductive lines while the semiconductor material was sputtered in an oxygen-rich plasma environment. It was discovered, however, that the problems could be solved by using a suitable alloy of titanium and tungsten for the conductive lines, because the oxides produced during semiconductor sputtering are electrically conductive or semiconductive to an extent that good electrical contact was formed. The titanium-tungsten lines can be plasma cleaned before semiconductor sputtering to remove any oxide formed since they were produced. In general, the conductive lines could include any metal, metal alloy, or other highly conductive material that results in good electrical contact formation.

The implementation of FIG. 17 thus illustrates an example of a device that includes a first layered structure with a support surface and a second layered structure on the support surface. The second layered structure includes first and second sets of thermal sensor components and bridge circuitry electrically connecting the first and second sets in a bridge. Each thermal sensor component has electrical resistivity that varies with temperature. Each of the first and second sets is capable of receiving respective thermal signals and the thermal signals received by the first set differ from those received by the second set. Each thermal sensor component has a lower surface disposed toward the support surface. The bridge circuitry is capable of receiving drive signals to allow electrical detection of difference between resistivities of the first and second sets of thermal sensor components, and the difference indicates difference between the respective thermal signals. The bridge circuitry includes, for each thermal sensor component, at least two sets of one or more electrically conductive portions that extend across and are in electrical contact with the thermal sensor component's lower surface.

The technique of producing the implementation of FIG. 17 illustrates a method of producing a detecting device, where the detecting device includes thermometer elements and bridge circuitry on a support layer. The method includes forming a patterned layer of conductive material over a supporting surface of the support layer, and the patterned layer of conductive material includes part of the bridge circuitry. The method also includes forming a patterned layer of semiconductor material over the part of the bridge circuitry. The patterned layer of semiconductor material includes the thermometer elements.

FIG. 18 shows a cross-section similar to that in FIGS. 13 and 17, illustrating a variation that could be applied either to the implementation of FIG. 13 or to the implementation of FIG. 17. Rather than showing the specific layers on polymer layer 1162, FIG. 18 simply shows schematically a pair of control/sensor elements 1310 within a general layer 1312. General layer 1312 can include several sublayers such as layers 1172 and 1174 in FIGS. 13 and 17 or other sublayers; the sublayers of general layer 1312 can perform various functions, by providing, for example, passivation, insulation, a hydrophobic or oleophobic top surface 1320, and so forth.

In this variation, elements 1314 and 1316 function both as components of thermal sensors and also as electrodes to control drop merging. In other words, in addition to the signals they may receive during detection of voltage across a bridge, elements 1314 and 1316 receive drop merge signals, such as a high voltage pulse with opposite polarity through the same conductive lines described above in relation to FIGS. 12-15 and 17. The circuitry connected to the conductive lines through the contact pads must therefore include appropriate protection for amplifier circuitry, such as a switch or other component to decouple the amps during the high voltage pulse, or some other circuitry to protect against electrostatic damage.

FIG. 18 illustratively shows protein drop 1330 and ligand drop 1332, both deposited on top surface 1320 of general layer 1312. Protein drop 1330 is deposited asymmetrically over the gap between elements 1314 and 1316 with a larger proportion of drop 1330 directly above element 1316 than the proportion above element 1314. Ligand drop 1332, on the other hand, is entirely above element 1314.

Signal source 1334 provides a high voltage pulse across elements 1314 and 1316. As described above in relation to FIG. 6, this causes drop 1330 to be propelled leftward toward stationary ligand drop 1332, causing the two drops to merge and mix.

The variation in FIG. 18 can be advantageous because separate drop merger electrodes are unnecessary, making it possible to increase the size of elements 1314 and 1316 as well as the other components in the thermal sensors and bridge circuitry without increasing the size of the cell. For example, semiconductor slabs with larger lengths and widths could be produced with the same resistance, such as by depositing a thinner layer of semiconductor material, a layer of semiconductor material with greater conductivity, or by patterning the conductive lines to have different spacings. As slab dimensions increase, small differences in slab length or width are proportionally smaller relative to total length or width; for example, if the fabrication technology allows a given width+0.5 μm, an increase in width from 100 to 500 μm reduces the percentage of error from 0.5% to 0.1%, which would assist in achieving a design goal of keeping a bridge's offset voltage below 0.1%. Therefore, the offset voltage of a bridge can be more easily reduced by making the slab sizes approximately equal.

The same advantage applies to the variation shown in FIG. 19, but it has the additional advantage that thermally conductive component 1160 has been omitted, making anti-coupling layer 1164 unnecessary. As a result, polymer layer 1162 can be somewhat thicker, as shown. For example, polymer layer 1162 could be a thicker layer of Kapton® or another polyimide layer. A significant advantage of using a thicker polymer layer is that fabrication is easier because there is less risk of tearing the polymer during handling. In other respects, the variation of FIG. 19 can be the same as FIG. 18, as described above.

The implementations of FIGS. 12-19 illustrate examples of devices, each of which includes a support layer. Two or more resistive thermometer elements are on the support layer, together with bridge circuitry. The bridge circuitry electrically connects first and second subsets of the thermometer elements in a bridge, and the bridge circuitry has one or more detection points. The bridge circuitry is capable of being driven to allow electrical detection, at the detection points, of differences between first and second temperature changes. The first temperature change is received by the first subset of the thermometer elements and the second temperature change is received by the second subset of the thermometer elements.

The technique of FIG. 15 and its modifications to produce structures as in FIGS. 17-19 illustrate examples of methods of producing detecting devices. The methods include producing resistive thermometer elements and bridge circuitry as described above. In particular, the thermometer elements and the bridge circuitry are produced on a support layer.

The array of FIG. 16, including cells implemented with detectors as in any of FIGS. 12-15, 17, 18, or 19, illustrates an example of an array with a support layer and not less than one detector on the support layer. Each detector includes two or more resistive thermometer elements on the support layer, together with bridge circuitry. The bridge circuitry electrically connects first and second subsets of the thermometer elements in a bridge, and the bridge circuitry has one or more detection points. The bridge circuitry is capable of being driven to allow electrical detection, at the detection points, of differences between first and second temperature changes. The first temperature change is received by the first subset of the thermometer elements and the second temperature change is received by the second subset of the thermometer elements.

The implementations of FIGS. 18 and 19 also illustrate examples of devices as described above in which the thermally isolated regions that include the first and second subsets of thermometer elements also include reaction surfaces. A reaction can occur on one of the reaction surfaces, producing reaction thermal change. The reaction surface is over the respective subset of thermometer elements, so that the temperature change received by the thermometer elements includes reaction thermal change from the reaction surface. The device also includes, below the reaction surface, a component that mixes fluids on the reaction surface, such as drop merging electrodes.

Figure 20:
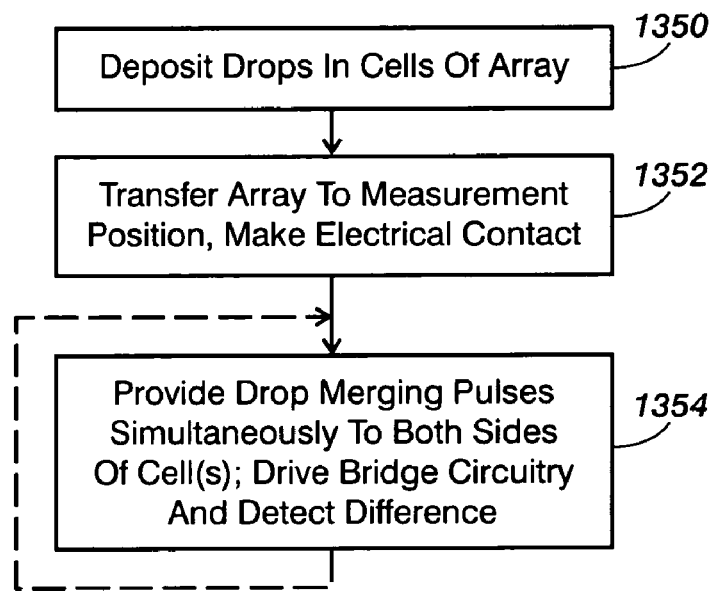
FIG. 20 is a flow chart showing operations in performing calorimetry with an array as in FIG. 16, implemented with cells as in any of FIGS. 12-15, 17, 18, or 19.

FIG. 20 illustrates general operations in performing calorimetry or a similar application of an array as in FIG. 16 with cells as described above in relation to FIGS. 12-15, 17, 18, or 19. In box 1350, drops are deposited on the surfaces of the measurement and reference sides of a set of cells in an array, with the drops being appropriately positioned over drop merging electrodes as described above. In box 1352, the array is transferred into a measurement position, and electrical contacts are made, such as with pogo pins being extended against contact pads of the array. Then, in box 1354, drop merging pulses are provided simultaneously to both sides of one or more cells, and the bridge circuitry of those cells is also driven to allow electrical detection of the difference between thermal signals received at the measurement and reference sides of each cell. As suggested by the dashed line around box 1354, the operation can be repeated as appropriate for any subset of the cells on which drops were deposited in box 1350; for example, the cells could be read out one by one, or other appropriate subsets could be read out, up to the case in which all cells are read out in parallel which may be possible if noise and intercell interference can be adequately controlled.

In the implementations described above, bridges illustratively have one terminal receiving an AC drive voltage and another connected to ground, but the same terminals could receive any other appropriate combination of voltages. For example, the terminal connected to ground could instead be connected to some other voltage different than the AC drive voltage, or the bridge could be driven by a balance transformer in which case the terminals are driven with opposite polarities relative to ground. Any of these variations would be within the scope of box 1354 in FIG. 20.

The technique of FIG. 20 illustrates another example of a method of using a device as described above. The method includes depositing drops of fluid on a reaction surface and a reference surface. The method also includes simultaneously activating drop merging electrodes in the regions that include the reaction surface and the reference surface to cause simultaneous reactions on the surfaces.

More generally, the implementations of FIGS. 12-20 are advantageous because they permit high sensitivity and high throughput in a label free calorimetric detection system, such as in proteomic and drug development research. Sensitivities as fine as single-digit microdegree resolution or better can be achieved, and the noise level of thermistors as described can approach the Johnson noise level. At the same time, other material properties that affect resolution are preserved, such as high TCR, thus improving the overall signal-to-noise ratio of an instrument. As a result, the array of FIG. 16 can advantageously be implemented to measure thermal change from merged drops with single digit micromolar concentrations of molecules.

The techniques described above are useful for calorimetry measurements, such as in biophysical and biochemical studies to determine energy changes as indications of biochemical reactions. Calorimetry measurements are useful in a broad variety of applications, including, for example, pharmaceuticals (drug discovery, decomposition reactions, crystallization measurements), biology (cell metabolism, drug interactions, fermentation, photosynthesis), catalysts (biological, organic, or inorganic), electrochemical reactions (such as in batteries or fuel cells), polymer synthesis and characterization, and so forth. In general, calorimetry measurements can be useful in the discovery and development of new chemicals and materials of many types, as well as in the monitoring of chemical processes.

In addition to calorimetry applications, techniques described above may be used in various other thermal sensing applications.

Some of the above exemplary implementations involve specific materials, such as amorphous silicon or vanadium oxide in thermistors; any of various polymers in a supporting layer; copper, aluminum, chromium, TiW, or a combination of them in conductive components; silicon oxynitride in barrier layers; and so forth, but the invention could be implemented with a wide variety of materials and with layered structures with various combinations of sublayers. In particular, other substrate materials such as silicon or other types of support structures could be used besides those specified above, and a wide variety of materials could be used in device layers, insulating layers, leads, lines, electrodes, and other components; for example, a top coating of sputter deposited $SiO_x$ or PECVD SiO or SiN could be provided. In addition, components could have various shapes, dimensions, or other numerical or qualitative characteristics other than those illustrated and described above.

Some of the above exemplary implementations involve two-dimensional arrays of thermal sensor cells with specified circuitry including circuitry connecting sensors as in a Wheatstone bridge and with a drop merging component, but the invention could be implemented with a single cell or with a one-dimensional array and with any suitable thermal sensor circuitry, with or without a drop merger and with sensors connected as in any appropriate type of bridge. In the above exemplary implementations, certain parts of a bridge take the form of bridge circuitry on the same support layer or surface as thermal sensors, but more or fewer components of the bridge could be on the same support layer or surface with the sensors. The above exemplary implementations generally involve cells with particular circuitry for other power and signal functions, but various other arrangements could be used.

The above exemplary implementations generally involve production and use of thermal sensors, devices, cells, and arrays following particular operations, but different operations could be performed, the order of the operations could be modified, and additional operations could be added within the scope of the invention. For example, as noted above, conductive lines could be formed before or after semiconductor slabs. Also, the positioning of components on the sides of a polymer layer or other support structure could be modified within the scope of the invention. During use, electrical signals could be provided to components in any appropriate sequence.

While the invention has been described in conjunction with specific exemplary implementations, it is evident to those skilled in the art that many other alternatives, modifications, and variations will be apparent in light of the foregoing description. Accordingly, the invention is intended to embrace all other such alternatives, modifications, and variations that fall within the spirit and scope of the appended claims.

What is claimed is:

1. A device comprising:
   a first layered structure with a support surface; and
   a second layered structure on the support surface, the second layered structure including:
      first and second pairs of thermal sensor components, each thermal sensor component having electrical resistivity that varies with temperature; each of the first pair of thermal sensing components and second pair of thermal sensing components each being capable of receiving respective thermal signals, with thermal signals received by the first pair of thermal sensing components differing from thermal signals received by the second pair of thermal sensing components; each thermal sensor component having a lower surface disposed toward the support surface; and
      bridge circuitry electrically connecting the first and second sets of thermal sensor components in a bridge; the bridge circuitry being capable of receiving drive signals to allow electrical detection of difference between resistivities of the first and second sets of thermal sensor components, the difference in resistivities indicating difference between respective thermal signals received by the first and second sets of thermal sensor components; the bridge circuitry including:
         for each thermal sensor component, at least two sets of one or more electrically conductive portions extending across and in electrical contact with the thermal sensor component's lower surface.

2. A device comprising:
   a first layered structure with a support surface; and
   a second layered structure on the support surface, the second layered structure including:
      first and second sets of thermal sensor components, each thermal sensor component having electrical resistivity that varies with temperature; the first set and second set each being capable of receiving respective thermal signals, with thermal signals received by the first set differing from thermal signals received by the second set; each thermal sensor component having a lower surface disposed toward the support surface; and
      bridge circuitry electrically connecting the first and second sets of thermal sensor components in a bridge; the bridge circuitry being capable of receiving drive signals to allow electrical detection of difference between resistivities of the first and second sets of thermal sensor components, the difference in resistivities indicating difference between respective thermal signals received by the first and second sets of thermal sensor components; the bridge circuitry including:

for each thermal sensor component, at least first and second sets of electrically conductive portions extending across and in electrical contact with the thermal sensor component's lower surface;

in the second layered structure, at least one of:

the conductive portions in the first set being electrically connected to each other on a first side of the thermal sensor component and the conductive portions in the second set being electrically connected to each other on a second side of the thermal sensor component opposite the first side; the first and second sets of conductive portions being interdigitated;

the conductive portions being formed from a first layer of material deposited over the support surface and the thermal sensor components being formed over the conductive portions; and the thermal sensor components including semiconductor material.

3. The device of claim 2 in which the conductive portions are formed from a first layer of material deposited over the support surface and the thermal sensor components are formed over the conductive portions.

4. The device of claim 2 in which the thermal sensor components include semiconductor material.

5. The device of claim 4 in which the conductive portions include a conductive material that has a conductive or semiconductive surface oxide layer providing electrical contact with the semiconductor material in the thermal sensor components.

6. The device of claim 5 in which the conductive material is an alloy of titanium and tungsten.

7. An array comprising:
a support layer;
not less than one detector on the support layer, each detector including:
two or more resistive thermometer elements; and
bridge circuitry electrically connecting first and second subsets of the thermometer elements in a bridge, each subset including one or more of the thermometer elements; the bridge circuitry having a set of one or more detection points; the bridge circuitry being capable of being driven to allow electrical detection, at the detection points, of difference between first and second temperature changes, the first temperature change being received by the first subset of the thermometer elements and the second temperature change being received by the second subset of the thermometer elements.

8. The array of claim 7 in which each thermometer element includes a semiconductor component with a lower surface disposed toward the support layer; the bridge circuitry including at least two sets of one or more electrically conductive portions extending across and in electrical contact with the semiconductor component's lower surface.

9. A device comprising:
a support layer;
on the support layer:
first, second, third, and fourth resistive thermometer elements; and
bridge circuitry electrically connecting the thermometer elements in a bridge; the bridge circuitry including first and second output points, first and second input points, and first, second, third, and fourth leads;

the first lead electrically connecting the first input point and the first and fourth thermometer elements; the second lead electrically connecting the first output point and the first and second thermometer elements;

the third lead electrically connecting the second input point and the second and third thermometer elements; the fourth lead electrically connecting the second output point and the third and fourth thermometer elements; the bridge circuitry being capable of being driven through the first and second input points to allow electrical detection, at the first and second output points, of difference between first and second temperature changes, the first temperature change being received by the first and third thermometer elements and the second temperature change being received by the second and fourth thermometer elements.

10. The device of claim 9 in which the support layer includes first and second regions that are substantially thermally isolated from each other, the first and third thermometer elements being in a first subset of thermometer elements and the second and fourth thermometer elements being in a second subset of thermometer elements, the first subset of the thermometer elements being on the first region and the second subset of the thermometer elements being on the second region; the device further comprising:

on the first region, a first thermally conductive structure having thermal contact with each of the first subset of the thermometer elements; and on the second region, a second thermally conductive structure having thermal contact with each of the second subset of the thermometer elements.

11. The device of claim 10 in which the support layer has first and second sides opposite each other; the first and second subsets of thermometer elements and the bridge circuitry being on the first side;

the first and second thermally conductive structures being on the second side.

12. The device of claim 10, further comprising:

on the first region, a reaction surface on which reactions occur, producing reaction thermal change; the first thermally conductive structure being in thermal contact with the reaction surface; the first temperature change including reaction thermal change from the reaction surface.

13. The device of claim 12, further comprising:

on the first region, a component that mixes fluids on the reaction surface; the reaction thermal change including heat of reaction between mixed fluids.

14. The device of claim 12 in which the second temperature change includes reference temperature change, the difference between the first and second temperature changes indicating difference between the reaction thermal change from the reaction surface and the reference temperature change.

15. The device of claim 14, further comprising:

on the second region, a reference surface exposed to the reference temperature change;

the second thermally conductive structure being in thermal contact with the reference surface.

16. The device of claim 15, further comprising:

on the first region, respective drop merging electrodes that mix fluids on the reaction surface; and on the second region, respective drop merging electrodes that mix fluids on the reference surface.

17. A method of using the device of claim 16, comprising:

depositing drops of fluids on the reaction surface and the reference surface; and simultaneously activating the drop merging electrodes in the first and second regions to cause simultaneous reactions on the reaction surface and the reference surface.

18. The device of claim 16, further comprising reaction control lines connected to the drop merging electrodes in the first and second regions; the reaction control lines being connected so that the drop merging electrodes in the first and second regions are simultaneously activated.

19. The device of claim 10 in which the first and second subsets of the thermometer elements are on left and right sides, respectively, of a symmetry axis extending across the support layer between the first and second regions; the first and second subsets being substantially symmetrical with respect to each other about the symmetry axis; the first and second thermally conductive structures being on the left and right sides, respectively, of the symmetry axis and being substantially symmetrical with respect to each other about the symmetry axis.

20. The device of claim 9 in which the support layer includes first and second regions that are substantially thermally isolated from each other, the first and third thermometer elements being in a first subset of thermometer elements and the second and fourth thermometer elements being in a second subset of thermometer elements, the first subset of the thermometer elements being on the first region and the second subset of the thermometer elements being on the second region; the device further comprising:
on the first region, a reaction surface on which reactions occur, producing reaction thermal change; the reaction surface being over the first subset of thermometer elements, the first temperature change including reaction thermal change from the reaction surface.

21. The device of claim 20, further comprising:
on the first region, below the reaction surface, a component that mixes fluids on the reaction surface; the reaction thermal change including heat of reaction between mixed fluids.

22. The device of claim 21 in which the component that mixes fluids includes drop merging electrodes.

23. The device of claim 9 in which the bridge's offset voltage is below the sensitivity limit for an application.

24. The device of claim 23 in which the thermometer elements are patterned from a first layer of material and the bridge circuitry includes a part patterned from a second layer of material; the thermometer elements and the part of the bridge circuitry being shaped and positioned so that the bridge's offset voltage is below the sensitivity limit despite process variations in patterning the first and second layers of material.

25. The device of claim 9 in which the first input point is an AC connection that connects to an AC generator, the second input point is a ground connection that connects to ground, and the first and second output points connect to detection circuitry that detects voltage difference between the first and second output points;
the voltage difference indicating difference between the first and second temperature changes.

26. A device comprising:
a first layered structure with a support surface; and
a second layered structure on the support surface, the second layered structure including:
first, second, third, and fourth thermal sensor components, each thermal sensor component having electrical resistivity that varies with temperature; and
bridge circuitry electrically connecting the thermal sensor components in a bridge; the bridge circuitry including first and second output points, first and second input points, and first, second, third, and fourth leads; the first lead electrically connecting the first input point and the first and fourth thermal sensor components; the second lead electrically connecting the first output point and the first and second thermal sensor components; the third lead electrically connecting the second input point and the second and third thermal sensor components; the fourth lead electrically connecting the second output point and the third and fourth thermal sensor components; the bridge circuitry being capable of being driven through the first and second input points to allow electrical detection, at the first and second output points, of difference between first and second thermal signals, the first thermal signal being received by the first and third thermal sensor components and the second thermal signal being received by the second and fourth thermal sensor components.

27. The device of claim 26 in which the first and third thermal sensor components are in a first set of thermal sensor components and the second and fourth thermal sensor components are in a second set of thermal sensor components; in electrical detection of difference between first and second thermal signals, the bridge circuitry receiving drive signals, the drive signals allowing electrical detection of difference between resistivities of the first and second sets of thermal sensor components, the difference in resistivities indicating difference between the first and second thermal signals.

28. The device of claim 26 in which each of the resistive thermometer elements includes:
a rectangular slab of semiconductive material with electrical resistance that varies in response to thermal change; the rectangular slab having first and second dimensions, first and second sides extending in the first dimension, and a contact surface between the first and second sides; and
first and second lead parts and first and second sets of digit lines, the digit lines in the first and second sets all extending across and being in electrical contact with the slab's contact surface, the first and second lead parts and the digit lines in the first and second sets all including conductive material; the digit lines in the first set overlapping the first side of the slab and connecting beyond the first side to the first lead part extending around the slab; the digit lines in the second set overlapping the second side of the slab and connecting beyond the second side to the second lead part extending around the slab; the first and second sets of digit lines together being interdigitated lines.

29. The device of claim 28 in which the digit lines in the first set also overlap the second side of the slab and the digit lines in the second set also overlap the first side of the slab.

30. The device of claim 28 in which, in each of the resistive thermometer elements, one of:
the slab's contact surface is an upper surface disposed away from the support surface; each digit line in the first and second sets being on the slab's upper surface; and
the slab's contact surface is a lower surface disposed toward the support surface; each digit line in the first and second sets being under the slab's lower surface.

31. The device of claim 28 in which the first and third thermal sensor components are in a first set of thermal sensor components and the second and fourth thermal sensor components are in a second set of thermal sensor components; the first and second sets of thermal sensor components being on left and right sides, respectively, of a symmetry axis extending across the support surface between first and second regions of the support surface that are substantially thermally isolated from each other; the first and second sets of thermal sensor components being on the first and second regions, respectively, and being substantially symmetrical with respect to each other about the symmetry axis; the slabs of thermal sensor components in each of the first and second sets having substantially identical first dimensions and substantially identical second dimensions; in each of the thermal sensor components, the digit lines in the first and second sets all being parallel to the symmetry axis.

32. The device of claim 31 in which thicknesses of the slabs in the first and second sets of thermal sensor components all differ by no more than 0.1%.

33. The device of claim 26 in which the first layered structure includes a layer of polymer material.

* * * * *